US012662437B2

(12) United States Patent
Kuechler et al.

(10) Patent No.: US 12,662,437 B2
(45) **Date of Patent: *Jun. 23, 2026**

(54) MEMBRANE-BASED SEPARATION PROCESSES ENHANCED WITH AN ABSORPTION DEVICE

(71) Applicant: ExxonMobil Chemical Patents Inc., Baytown, TX (US)

(72) Inventors: Keith H. Kuechler, Friendswood, TX (US); Pavel V. Kortunov, Flemington, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 158 days.

This patent is subject to a terminal disclaimer.

(21) Appl. No.: 18/681,161

(22) PCT Filed: Jul. 25, 2022

(86) PCT No.: PCT/US2022/038134
§ 371 (c)(1),
(2) Date: Feb. 5, 2024

(87) PCT Pub. No.: WO2023/022847
PCT Pub. Date: Feb. 23, 2023

(65) Prior Publication Data
US 2024/0279141 A1　Aug. 22, 2024

Related U.S. Application Data

(60) Provisional application No. 63/234,993, filed on Aug. 19, 2021.

(51) Int. Cl.
*C07C 7/144* (2006.01)
*B01D 11/04* (2006.01)
(Continued)

(52) U.S. Cl.
CPC .......... *C07C 7/144* (2013.01); *B01D 11/0415* (2013.01); *B01D 61/246* (2013.01); *C07C 7/11* (2013.01); *B01D 2311/08* (2013.01)

(58) Field of Classification Search
CPC ........ C07C 7/144; C07C 7/11; B01D 11/0415
See application file for complete search history.

(56) References Cited

U.S. PATENT DOCUMENTS 4,174,353 A　11/1979　Marcinkowsky et al.
4,283,255 A　8/1981　Ramshaw et al.
(Continued)

OTHER PUBLICATIONS

"Separation and Purification Technology / Edition 1," edited by Norman N. Li, Joseph M. Calo, Publisher: Taylor & Francis, Jul. 21, 1992; Chapter 3: Olefin Recovery and Purification via Silver Complexation, Keller, et al., pp. 59-83.
(Continued)

*Primary Examiner* — Tam M Nguyen
(74) *Attorney, Agent, or Firm* — WOMBLE BOND DICKINSON (US) LLP; Kevin Davis

(57) ABSTRACT

A salt ion membrane may be paired with an absorption device to provide advantaged separation processes comprising: introducing a first aqueous salt stream and a mixed feed stream comprising at least one olefin and at least one paraffin to a salt ion membrane under conditions effective to form at least two phases; obtaining an olefin-rich permeate stream and an olefin-lean retentate stream from the salt ion membrane, in which the olefin-rich permeate stream and/or the olefin-lean retentate stream further comprises a salt ion membrane aqueous salt phase; introducing at least a portion of the olefin-lean retentate stream and a second aqueous salt stream to an absorption device under conditions effective to promote olefin extraction; obtaining an olefin-rich aqueous salt stream from the absorption device; and providing at
(Continued)

least a portion of the olefin-rich aqueous salt stream as at least a portion of the first aqueous salt stream.

27 Claims, 8 Drawing Sheets

(51) Int. Cl.
B01D 61/24 (2006.01)
C07C 7/11 (2006.01)

(56) References Cited

U.S. PATENT DOCUMENTS

| | | | | |
|---|---|---|---|---|
| 5,107,058 | A * | 4/1992 | Chen | C07C 7/144 |
| | | | | 585/818 |
| 6,395,952 | B1 | 5/2002 | Barchas | |
| 6,518,476 | B1 | 2/2003 | Culp | |
| 7,361,800 | B2 | 4/2008 | Herrera et al. | |
| 8,899,557 | B2 | 12/2014 | Cullinane et al. | |
| 9,782,724 | B2 | 10/2017 | Feng et al. | |
| 10,258,929 | B2 | 4/2019 | Liu et al. | |
| 10,507,435 | B1 | 12/2019 | Frey | |
| 2011/0077446 | A1 * | 3/2011 | Shanbhag | B01D 53/72 |
| | | | | 585/818 |
| 2012/0190905 | A1 | 7/2012 | Gorke | |
| 2018/0093230 | A1 | 4/2018 | Koizumi | |
| 2021/0403397 | A1 * | 12/2021 | Liu | B01D 53/228 |
| 2022/0016575 | A1 * | 1/2022 | Suwan | C07C 7/04 |
| 2024/0139672 | A1 * | 5/2024 | Aslam | B01D 69/02 |

OTHER PUBLICATIONS

Rami Faiz et al: "Olefin/paraffin separation using membrane based facilitated transport/chemical absorption techniques", Chemical Engineering Science, Oxford, GB, vol. 73, Jan. 18, 2012 (Jan. 18, 2012), pp. 261-284.
Ind. Eng. Chem. Res. 2004, 43, 1150-1162, Rao, et al., "Process Intensification in Rotating Packed Beds (HIGEE): An Appraisal".

* cited by examiner

MEMBRANE-BASED SEPARATION PROCESSES ENHANCED WITH AN ABSORPTION DEVICE

CROSS-REFERENCE TO RELATED APPLICATIONS

This application is a US national phase application of PCT Application Serial No. PCT/US2022/038134 having a filing date of Jul. 25, 2022, which claims priority to and the benefit of U.S. Provisional Application No. 63/234,993 having a filing date of Aug. 19, 2021, the disclosures of all of which are incorporated herein by reference in their entireties.

FIELD

The present disclosure relates to hydrocarbon separation processes and, more particularly, membrane-based processes for separating at least one olefin from at least one paraffin.

BACKGROUND

Olefinic hydrocarbons (olefins) are among the world's most useful chemical components. Ethylene and propylene are among the highest volume petrochemical products used in chemical production, while 1-butene (butene-1), isobutylene, and isoamylene are widely used as petrochemical products and as intermediates in the production of motor gasoline. Similarly, olefinic hydrocarbons having from 6 to 12 carbon atoms are also useful petrochemical products, including as motor gasoline blend components, given their considerably higher octane value compared to their paraffinic hydrocarbon counterparts of the same carbon number.

Olefins may be produced by thermal or catalytic reactions of a wide range of naturally occurring hydrocarbon feedstocks, including natural gas (predominantly methane), ethane, propane, butanes, pentanes, liquid petroleum fractions including naphtha and atmospheric gas oil, and even whole crude with gaseous hydrocarbons removed. Historically, the dominant processes in industry have involved cracking chemistry, such as Steam Cracking and Fluidized Catalyst Cracking. More recently, processes have been commercialized to produce light olefins like propylene and butenes through catalytic dehydrogenation of their corresponding paraffins, i.e., propane and n-butane.

Olefin production processes may create a desired olefin in combination with a considerable concentration of many other hydrocarbon species ranging from simple paraffins like methane to complex hydrocarbons like multi-ring aromatic compounds. Heteroatomic compounds may also be produced in some cases, typically if one or more heteroatoms was present in a hydrocarbon feedstock or present in the reaction conditions used to produce the olefin. Paraffins having the same number of carbon atoms as a desired olefin or having one carbon atom more or less than a desired olefin may be commonly produced, although an even wider breadth of paraffins may frequently occur, oftentimes in combination with additional olefins as well. Residual paraffins from a hydrocarbon feedstock may also be present. For example, Steam Cracking of an ethane feedstock may afford a C2 stream comprising about 60-80 wt % ethylene and about 20-40 wt % ethane, while a naphtha feedstock may afford a C2 stream comprising about 80-90 wt % ethylene and about 10-20 wt % ethane in combination with a C3 stream comprising about 85-95 wt % propylene and about 5-15 wt % propane. Catalytic dehydrogenation of propane may afford a C3 stream comprising about 30-60 wt % propylene and about 40-70 wt % propane.

While olefins may be used to create many types of products, their largest use is in polymer synthesis, where high-purity ethylene and propylene feedstocks may be highly desired. For example, the minimum ethylene purity for polyethylene production may be about 99.9 wt %, or even about 99.95 wt %, with the balance of materials being paraffin compounds including methane, ethane and propane, for example. Similarly, the minimum propylene purity for creating polypropylene polymers and copolymers may be at least about 99.5 wt %, again with the balance of materials usually being paraffins. There may be additional limitations on olefin purity such as, for example, heteroatomic compound amounts less than 100 ppm by weight relative to olefin, highly unsaturated hydrocarbons such as dienes or acetylenes less than 100 ppm by weight relative to olefin, and less than 100 ppm by weight olefins other than a desired olefin (e.g., propylene and butenes in ethylene, and ethylene, butenes and pentenes in propylene).

Thus, separation of olefins from paraffins is among the most widely practice separations in the petrochemical industry, especially from paraffins having the same number of carbon atoms or paraffins within one carbon atom of a desired olefin. Such separations have conventionally been conducted by fractional distillation processes that may be very energy intensive and necessitate a large capital equipment investment. For example, separation of ethylene from ethane may utilize a distillation column having about 130 theoretical plates and a reflux ratio of about 6, and that is conducted at a distillation temperature of about −20° C. or below, which may necessitate use of an expensive refrigeration system. Separation of propylene from propane via distillation may be conducted above ambient temperatures but utilize a distillation column having as many as about 200 theoretical plates and a reflux ratio of about 11-17. For reference, ethylene and propylene distillation processes may produce polymer-grade ethylene and propylene with purities of about 99.9 wt % and about 99.5 wt %, respectively, at a recovery of olefins from a hydrocarbon feed of up to about 99.9 wt % and about 99.0 wt %, respectively for ethylene and propylene, even from hydrocarbon feedstocks having an olefin concentration as low as about 30 wt %. Usually, the higher the carbon number, the more energy intensive and expensive the separation of an olefin from its corresponding paraffin becomes. As such, large-scale separation of olefins larger than propylene by distillation may become cost- and energetically prohibitive.

Membranes are an emerging technology for the separations of olefins from paraffins. Although various membrane technologies have been developed, "facilitated transport" membranes are among those with high promise for large-scale commercial applications. Such facilitated transport membranes may feature a copper or silver salt as a cationic constituent embedded within a membrane material in the presence of water, either as a vapor or as a liquid, leading such membranes to be referred to herein as "salt ion membranes." Non-limiting examples of such facilitated transport membranes are disclosed in U.S. Patent Application Publication 2018/0093230, and U.S. Pat. Nos. 9,782,724 and 10,507,435, each of which is incorporated herein by reference. Illustrative facilitated transport membrane may employ a porous membrane material comprising a hydrophilic polymer such as chitosan, hyaluronic acid and/or sodium alginate, in which the cationic constituent of the salt resides. Hydrophilic polymers such as these may afford good olefin-paraffin separation selectivity in the presence of water, which may be in a liquid phase and/or a vapor phase.

Facilitated transport membranes are not without their difficulties, however. Like any membrane operating with a pressure drop through the membrane material (in this case, the partial pressure of the olefin), the pressure drop is the only driving force for promoting separation. As chemical potentials equalize, the separation eventually runs out of driving force to carry an olefin over to a permeate side of the membrane material. Thus, for a single membrane stage, one may achieve either a relatively high recovery of the olefins from a hydrocarbon feed with a modest olefin purity, or incomplete recovery of the olefins a hydrocarbon feed but with high olefin purity. Further, the lower the olefin concentration in a given hydrocarbon feed, the lower the olefin recovery that can be practically achieved at a specified olefin purity. This dichotomy is the single greatest disadvantage of membrane separation technologies and is the primary reason they have seen so little industrial application to date. As noted above, olefin syntheses are often complicated and expensive, and high-purity olefins obtained in high yield are needed for many applications, conditions which single-stage membrane separations are presently unable to provide.

By way of example, U.S. Pat. No. 10,507,435 describes a membrane-based olefin separation process that provides propylene at 99.5 wt % purity, but only at about 70 wt % recovery from a hydrocarbon feed containing a relatively high loading of propylene (70 wt % in hydrocarbon feed), an undesirable amount of yield loss in most circumstances. While olefin recovery may be improved using multiple membranes in "membrane cascades," again as described in U.S. Pat. No. 10,507,435, such cascades may be expensive to build and operate relative to a single membrane stage. For example, a substantially larger membrane contact area may be needed in downstream membrane stages, especially for ethylene, propylene, butenes, or pentenes separations. In addition, to keep the olefin partial pressure sufficiently high throughout the membrane cascade, expensive and energy-intensive compressors may be needed to circulate low pressure, vapor-phase permeate from downstream membrane stages to an upstream membrane stage.

Another alternative for separating olefins from paraffins involves contacting an aqueous salt solution, such as an aqueous copper or silver salt, with a hydrocarbon feed containing one or more olefins, in essentially an extractive separation process. Without being bound by theory or mechanism, a cationic portion of the metal salt is believed to form an olefin pi-bond complex that is of significantly lower volatility than the corresponding paraffins, which do not form a pi-bond complex and thus allows ready separation of the paraffins from the olefins. Aqueous silver nitrate has been studied in particular depth, especially for ethylene and ethane, as described in U.S. Pat. Nos. 4,174,353 and 6,395,952, incorporated herein by reference, and "Separation and Purification Technology/Edition 1," edited by Norman N. Li, Joseph M. Calo, Publisher: Taylor & Francis, Jul. 21, 1992; Chapter 3: Olefin Recovery and Purification via Silver Complexation, Keller, et al. While such complexation-based extractive separation technologies may avoid some of the problems of conventional olefin distillations while achieving similar olefin recovery and purity, capital equipment and operating expenses are still significant concerns. Moreover, a large metal salt inventory is often needed, particularly outside of an absorption column where contact takes place to form the complex, such as within a vent column, heat exchangers, and a stripping column. Further, recycling of vent column vapor to the absorption column may be conducted to improve olefin recovery and may utilize a compressor, thereby increasing process complexity and capital equipment needs still further.

SUMMARY

In various aspects, the present disclosure provides processes comprising: providing a mixed feed stream comprising at least one olefin and at least one paraffin; introducing at least a first portion of the mixed feed stream and a first aqueous salt stream to a salt ion membrane under conditions effective to form at least two phases while contacting the salt ion membrane; wherein the salt ion membrane is more permeable to olefins than to paraffins; obtaining an olefin-rich permeate stream and an olefin-lean retentate stream from the salt ion membrane, the olefin-lean retentate stream comprising at least a portion of the at least one olefin from the mixed feed stream; wherein at least one of the olefin-rich permeate stream and the olefin-lean retentate stream further comprises a salt ion membrane aqueous salt phase; introducing at least a portion of the olefin-lean retentate stream and a second aqueous salt stream to an absorption device under conditions effective to promote olefin extraction into the second aqueous salt stream; obtaining from the absorption device an olefin-rich aqueous salt stream comprising at least a portion of the at least one olefin from the olefin-lean retentate stream, and an olefin-lean hydrocarbon stream comprising at least a portion of the at least one paraffin from the mixed feed stream; and providing at least a portion of the olefin-rich aqueous salt stream as at least a portion of the first aqueous salt stream.

These and other features and attributes of the disclosed methods and compositions of the present disclosure and their advantageous applications and/or uses will be apparent from the detailed description which follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

To assist one of ordinary skill in the relevant art in making and using the subject matter hereof, reference is made to the appended drawings, wherein.

DETAILED DESCRIPTION

Figure 1A:
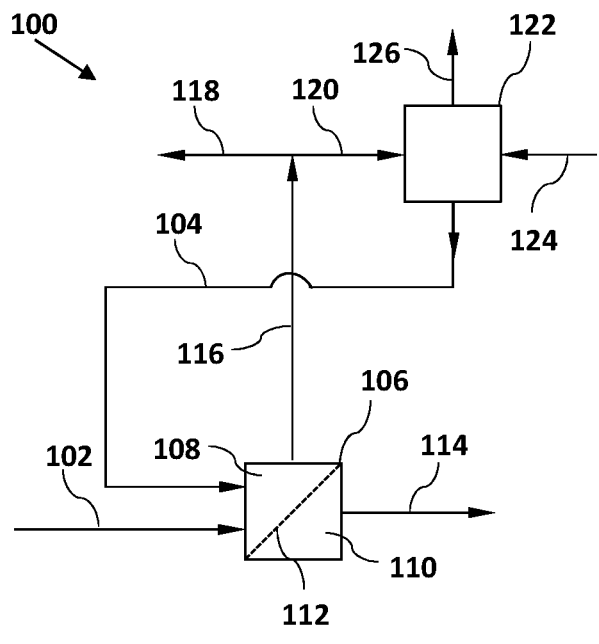
FIGS. 1A and 1B are block diagrams showing an olefin separation process of the present disclosure, in which a second aqueous salt stream is externally supplied.

The present disclosure relates to hydrocarbon separation processes and, more particularly, membrane-based processes for separating at least one olefin from at least one paraffin.

Definitions

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process may be described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite articles "a" or "an" shall mean "at least one" unless specified to the contrary or the context clearly indicates otherwise. Thus, for example, embodiments using "a fractionation column" include embodiments where one, two or more fractionation columns are used, unless specified to the contrary or the context clearly indicates that only one fractionation column is used.

As used herein, the term "consisting essentially of" means a composition, feed, stream or effluent that includes a given component or group of components at a concentration of at least about 60 wt %, preferably at least about 70 wt %, more preferably at least about 80 wt %, more preferably at least about 90 wt %, or still more preferably at least about 95 wt %, based on the total weight of the composition, feed, stream or effluent.

The following abbreviations may be used herein for the sake of brevity: RT is room temperature (and is 23° C. unless otherwise indicated), kPag is kilopascal gauge, psig is pound-force per square inch gauge, barg is bar gauge, psia is pounds per square inch absolute, and WHSV is weight hourly space velocity.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

As used herein, the term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of such at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

As used herein, an "aromatic hydrocarbon" is a hydrocarbon comprising an aromatic ring in the molecule structure thereof. An aromatic compound may have a cyclic cloud of pi electrons meeting the Hückel rule. A "non-aromatic hydrocarbon" means a hydrocarbon other than an aromatic hydrocarbon.

An "effluent" or a "feed" is sometimes also called a "stream" in this disclosure. Where two or more streams are shown to form a joint stream and then supplied into a vessel, it should be interpreted to include alternatives where the streams are supplied separately to the vessel where appropriate. Likewise, where two or more streams are supplied separately to a vessel, it should be interpreted to include alternatives where the streams are combined before entering into the vessel as joint stream(s) where appropriate.

The term "selectivity" refers to the degree to which a particular reaction forms a specific product, rather than another product, or the degree to which a separation process separates a specific component from another component, rather than the other component being retained with the specific component. Selectivity is based on the product formed or separated, regardless of the conversion/yield of a particular reaction or the extent of separation of a component of interest from a mixture. The selectivity for a given component can be defined as weight percent (wt %) of that component relative to the total weight of other components that are formed or separated with a component of interest.

As used herein, the term "liquid-phase" means separation conditions in which a stream is substantially in liquid phase. "Substantially in liquid phase" means ≥90 wt %, preferably ≥95 wt %, preferably ≥99 wt %, and preferably the entirety of the stream is in liquid phase.

As used herein, the term "vapor-phase" means separation conditions in which a stream is substantially in vapor phase. "Substantially in vapor phase" means ≥90 wt %, preferably ≥95 wt %, preferably ≥99 wt %, and preferably the entirety of the stream is in vapor phase.

As used herein, the term "rich" or "enriched," when describing a component in a stream, means that the stream comprises the component at a concentration higher than a source material from which the stream is derived. As used herein, the term "depleted" or "lean," when describing a component in a stream, means that the stream comprises the component at a concentration lower than a source material from which the stream is derived.

Unless otherwise specified herein, any stream herein that is "rich" in a particular component may "consist of" or "consist essentially of" that component. "Consisting essentially of," as used herein, means that a composition, feed, stream or effluent comprises a given component at a concentration of at least about 60 wt %, preferably at least about 70 wt %, more preferably at least about 80 wt %, more preferably at least about 90 wt %, still more preferably at least about 95 wt %, based on the total mass of the composition, feed, stream or effluent in question.

Unless otherwise specified herein, any stream that is "lean" in a particular component may be "free of" or "substantially free of" that component. "Essentially free of" and "substantially free of," as interchangeably used herein, mean that a composition, feed, stream or effluent comprises a given component at a concentration of at most about 10 wt %, preferably at most about 8 wt %, more preferably at most about 5 wt %, more preferably at most about 3 wt %, still more preferably at most about 1 wt %, based on the total mass of the composition, feed, stream or effluent in question.

Olefin Separation Processes

As discussed above, separation of a hydrocarbon feed comprising a mixture of at least one olefin and at least one paraffin may be problematic. Distillation processes may be energy-intensive and cost-prohibitive, including large capital equipment investments. Complexation-based separations have not yet progressed to a point of economic viability. Membrane-based separations using a single membrane are unable to simultaneously afford high olefin purity and high olefin recovery, and membrane cascades may be expensive and complicated to implement.

The present disclosure provides advantaged separation processes for separating a feed mixture comprising at least one olefin and at least one paraffin, referred to herein as a "mixed feed stream." In particular, the separation processes disclosed herein couple membrane-based separation (e.g., using a facilitated transport membrane, such as a salt ion membrane) with olefin complexation aspects of extractive separation using a suitable metal salt. That is, the separation processes disclosed herein may enhance or augment membrane-based separation of at least one olefin from at least one paraffin with an absorption device that promotes contact of one or more olefins with an aqueous salt solution capable of forming a complex with one or more olefins. As disclosed herein, a salt ion membrane may facilitate olefin recovery in high purity, even though a low recovery of olefins may occur, and an absorption device may facilitate recovery of olefins otherwise not recovered from a permeate side of the salt ion membrane. Accordingly, the processes disclosed herein may achieve both high olefin purity and high recovery with a single membrane stage and a single absorption device.

The separation processes disclosed herein are based upon the recognition that an aqueous salt solution suitable to promote olefin complexation also may contact a salt ion membrane to promote separation therein as well, thereby allowing the membrane separation process and the complexation process to be effectively coupled together with one another. When coupled together appropriately, as discussed in further detail herein, the salt ion membrane may promote high-purity separation of at least one olefin from at least one paraffin, and the absorption device and its associated aqueous salt solution may increase the extent of recovery of at least one olefin. An aqueous salt solution that both contacts a salt ion membrane and is used for promoting olefin complexation in an absorption device may be referred to herein as a "salt ion membrane aqueous salt phase." As such, the present disclosure advantageously overcomes the primary difficulties associated with conventional membrane-based and extraction-based olefin separation processes, while providing energetic advantages over conventional distillation-based olefin separation technologies.

In addition to facilitating advantaged separation of at least one olefin from at least one paraffin with both high olefin recovery and purity, the separation processes disclosed herein may offer numerous other advantages as well, as discussed in greater detail hereinafter. Foremost, the separation processes disclosed herein are readily configurable to convey the salt ion membrane aqueous salt phase from the salt ion membrane to an absorption device in various manners depending on process-specific factors, such as whether the salt ion membrane aqueous salt phase is primarily transferred across the salt ion membrane (e.g., in a permeate stream) or retained without being transferring across the salt ion membrane (e.g., in a retentate stream). When located in the retentate stream, the salt ion membrane aqueous salt phase may be at least partially separated from one or more olefins in the retentate stream before being circulated to the absorption device for promoting olefin complexation, or the salt ion membrane aqueous salt phase may be conveyed directly within an olefin-lean retentate stream to the absorption device. Salt ion membrane aqueous salt phase may likewise be separated from the permeate stream before being circulated to the absorption device. Further, a permeate stream and/or a retentate stream obtained from the salt ion membrane, or a salt ion membrane aqueous salt phase obtained therefrom, may be further processed (conditioned) to increase or decrease an olefin concentration or olefin absorption capacity as process needs dictate. Particular process configurations are discussed in greater detail hereinbelow in reference to the drawings.

Moreover, the separation processes disclosed herein may be conducted with a one-to-one ratio of salt ion membrane and separation device, which may afford capital equipment savings and process simplification relative to membrane cascades employing multiple membranes. Preferably, the separation processes may be conducted with one salt ion membrane and one absorption device in a given process stream. Of course, multiple process streams may be separated in parallel, if desired, with one salt ion membrane and one absorption device being housed in each process stream.

Further advantageously, the separation processes disclosed herein may circulate the salt ion membrane aqueous salt phase and any complexed olefins contained therein as a liquid stream. Circulation of complexed olefins as a liquid stream may provide significant advantages over circulating or recycling gas streams or mixed gas-liquid streams comprising one or more uncomplexed olefins. Liquid circulation pumps capable of circulating a liquid stream are considerably less complex and less expensive to operate than are compressors and like capital equipment needed to pressurize a gas stream into a state suitable for circulation.

According to various embodiments of the present disclosure, separation processes disclosed herein may comprise: providing a mixed feed stream comprising at least one olefin and at least one paraffin; introducing at least a first portion of the mixed feed stream and a first aqueous salt stream to a salt ion membrane under conditions effective to form at least two phases while contacting the salt ion membrane; obtaining an olefin-rich permeate stream and an olefin-lean retentate stream from the salt ion membrane, the olefin-lean retentate stream comprising at least a portion of the at least one olefin from the mixed feed stream; wherein at least one of the olefin-rich permeate stream and the olefin-lean retentate stream further comprises a salt ion membrane aqueous salt phase; introducing at least a portion of the olefin-lean retentate stream and a second aqueous salt stream to an absorption device under conditions effective to promote olefin extraction into the second aqueous salt stream; obtaining from the absorption device an olefin-rich aqueous salt stream comprising at least a portion of the at least one olefin from the olefin-lean retentate stream, and an olefin-lean hydrocarbon stream comprising at least a portion of the at least one paraffin from the mixed feed stream; and providing at least a portion of the olefin-rich aqueous salt stream as at least a portion of the first aqueous salt stream. As discussed in further detail herein, the salt ion membrane is more permeable to olefins than to paraffins. Additional details in regard to the foregoing are provided hereinafter.

The second aqueous salt stream introduced to the absorption device may comprise at least a portion of the salt ion membrane aqueous salt phase. The salt ion membrane aqueous salt phase introduced to the absorption device may be sourced from the olefin-rich permeate stream and/or the olefin-lean retentate stream, as discussed further hereinbelow. In particular, the salt ion membrane aqueous salt phase introduced to the absorption device as at least a portion of the second aqueous salt stream may be separated from the olefin-rich permeate stream and/or the olefin-lean retentate stream before being provided as the at least a portion of the second aqueous salt stream. In more specific examples, the olefin-rich permeate stream may further comprise at least a portion of the salt ion membrane aqueous salt phase, and at least a portion of the second aqueous salt stream may be obtained from the salt ion membrane aqueous salt phase comprising the olefin-rich permeate stream. In other examples, the olefin-lean retentate stream may comprise at least a portion of the salt ion membrane aqueous salt phase, and at least a portion of the second aqueous salt stream may be obtained from the salt ion membrane aqueous salt phase comprising the olefin-lean retentate stream. Further details are provided hereinbelow in reference to the drawings.

Mixed feed streams separable according to the disclosure herein may be a hydrocarbon feed obtained from any source and comprise a mixture of at least one olefin and at least one paraffin. A plurality of olefins and/or a plurality of paraffins may be present in various instances. The at least one olefin may comprise one or more of ethylene, propylene, or one or more higher olefins having least 4 and no greater than about 12 carbon atoms. The higher olefins may be straight-chain (normal or linear) or branched, and an olefin moiety therein may be present at any position within the olefin. Linear alpha olefins (LAOs), including ethylene and/or propylene, and/or internal olefins or vinylidene olefins may be separable from one or more paraffins according to the disclosure herein. Mixtures of more than one type of olefin may be present in the mixed feed stream, including any combination of olefins having differing numbers of carbon atoms and/or olefin isomers (geometric and/or positional isomers), including branched olefins, linear olefins, and differing double bond locations.

Similarly, the one or more paraffins within the mixed feed stream may comprise one or more of methane, ethane, propane, and one or more higher paraffins having at least 4 and no greater than about 12 carbon atoms. Higher paraffins may be linear and/or branched, and the mixed feed stream may comprise any combination of linear paraffins, branched paraffins, cyclic paraffins, and/or paraffins having differing numbers of carbon atoms. The mixed feed stream may comprise one paraffin isomer or multiple paraffin isomers for a given number of carbon atoms. Mixtures of more than one type of paraffin may be present in the mixed feed stream, including any combination of paraffins having differing numbers of carbon atoms and/or paraffin isomers, including branched paraffins, cyclic paraffins, and/or linear paraffins.

Optionally, the mixed feed stream may comprise a gas, such as nitrogen, argon, or any combination thereof.

Further optionally, the mixed feed stream may comprise one or more contaminants, which may interact with the cationic substituent of the metal salt within the salt ion membrane and/or the various aqueous salt streams contacted with one or more components of the mixed feed stream. If present, the concentration of the one or more contaminants may be about 10 wppm or below, or about 1 wppm or below, each based on total mass of the mixed feed stream. Contaminants that may be present include, but are not limited to, hydrogen, hydrocarbons containing an acetylene moiety, heteroatomic organic compounds, heteroatomic species including sulfur, oxygen, mercury or arsenic atoms or ions, such as elemental dioxygen ($O_2$), heteroatom hydrides, (e.g., hydrogen sulfide ($H_2S$) and arsine ($AsH_3$)), or within a carbonaceous compound (e.g., carbon monoxide (CO), carbon dioxide ($CO_2$), ethyl mercaptan ($CH_3CH_2SH$) or thiophene ($C_4H_4S$)).

If needed, the mixed feed stream may be purified to remove one of more components or contaminants that may interfere with the separation processes disclosed herein. Suitable purification processes may be determined by the type(s) of components or contaminants that are present and will be familiar to persons having ordinary skill in the art.

The mixed feed stream may be provided to the salt ion membrane as a vapor, a liquid, or a combination thereof in any ratio of vapor to liquid. The temperature of the mixed feed stream when contacting the salt ion membrane may range from about 5° C. to about 80° C., or from about 20° ° C. to about 70° ° C., or from about 40° C. to about 65° C. The pressure of the mixed feed stream may range from about 2 bar to about 40 bar, or about 5 bar to about 30 bar, or about 8 bar to about 25 bar.

The concentration of olefins in the mixed feed stream may range from about 1 wt % to about 99 wt %, or about 5 wt % to about 95 wt %, or about 10 wt % to about 90 wt %, each based on total mass of the mixed feed stream. Paraffins may constitute the balance of the mixed feed stream, and thus may comprise at least about 1 wt % and no greater than about 99 wt % of the mixed feed stream.

The first and second aqueous salt streams may each comprise a metal salt capable of forming a complex with the at least one olefin. The metal salt may comprise a copper salt, a silver salt, or any combination thereof, such as a Ag (I) salt, a Cu (I) salt, or any combination thereof. Suitable anion forms for the metal salt may include but are not limited to, nitrate, chlorate, tetrafluoroborate, and trifluoroacetate anion, preferably nitrate. Both the first and second aqueous salt streams may comprise silver nitrate in particular examples. The concentration of metal salt in the first and second aqueous salt streams may range from about 0.5 M to about 10 M, or about 1 M to about 9 M, or about 3 M to about 8 M.

Compositionally, the first and second aqueous salt streams may be similar to one another and comprise the same metal salt(s), with the exception that the second aqueous salt stream may have a lower olefin concentration than does the first aqueous salt stream (unless both the first and second aqueous salt streams comprise substantially no olefins). More typically, both the first and second aqueous salt streams comprise at least some olefins, and the second aqueous salt stream has a lower olefin concentration. At least a portion of the second aqueous salt stream may comprise a salt ion membrane aqueous salt phase obtained from the olefin-lean retentate stream and/or the olefin-rich permeate stream, optionally after further conditioning thereof.

The olefin concentration of the first and second aqueous salt streams may depend on the nature of and conditions within the absorption device, as well as conditions outside the absorption device and further processing taking place outside the absorption device. Factors influencing the olefin concentration in the first and second aqueous salt streams may include, for example, temperature, pressure, number of extraction stages, concentration of the metal salt, particularly the concentration of the metal salt in the second aqueous salt stream provided to the absorption device, the olefin concentration in the olefin-lean retentate stream provided to the absorption device, and the relative mass rates of introduction of the second aqueous salt stream and the olefin-lean retentate stream introduced to the absorption device.

A concentration of olefins in the first and second aqueous salt streams may range from about 0.5 mol % to about 20.0 mol % within the condition ranges described herein. The olefin concentration may also depend upon the particular olefin(s) that is/are present in the mixed feed stream, as each may have its own distinct equilibrium behavior. For example, at 30° C. and 10 bar in a 7 M solution of silver nitrate, the solubility of ethylene is about 9 mol %, while the solubility of propylene is about 11 mol %. At 30° C. and 3 bar in a 4 M solution of silver nitrate, the solubility of propylene is about 3 mol %, while the solubility of 1-butene is about 5 mol %. The pressure in these examples is with reference to a single, pure olefin in a vapor phase. Mixtures of olefins may adhere to the equilibrium value for each pure component according to its specific concentration in the mixed feed stream.

In addition to one or more olefins, the first and second aqueous salt streams may also comprise one or more paraffins. When present, the one or more paraffins may be present at a concentration that is at least an order of magnitude lower than that of the one or more olefins, due primarily to the phase equilibria of these compounds and the lack of complexation of the one or more paraffins by the metal salt. Otherwise, factors affecting the paraffin concentrations in the first and second aqueous salt streams are similar to those described above for olefins. In addition, the first and second aqueous salt streams optionally may comprise one or more of the contaminants that may be present in the mixed feed stream.

Conditions effective to form at least two phases while contacting the salt ion membrane may include any combination of conditions that result in the mixed feed stream and the first aqueous salt stream forming two or more different phases. The mixed feed stream and the first aqueous salt stream contacting the salt ion membrane may form two liquid phases, a liquid phase and a gas phase, or two gas phases. Three or more phases may be present in some instances. Additional details are provided below.

Salt ion membranes suitable for use in the disclosure herein are facilitated transport membranes that comprise at least one metal salt within their membrane structure. Examples of suitable salt ion membranes are described in U.S. Pat. Nos. 10,507,435; 10,258,929; 9,782,724; and 7,361,800, and U.S. Patent Application Publication 2018/0093230, each of which is incorporated herein by reference. Other suitable salt ion membranes are described in further detail in U.S. Pat. No. 10,569,233 and U.S. Patent Application Publications 2017/0354918, 2018/0001277, and 2018/0001268, each of which are also incorporated herein by reference as well. The at least one metal salt associated with the membrane structure may also be a metal salt suitable for incorporation in the first and second aqueous salt streams for promoting olefin complexation. Additional salt ion membrane details follow hereinafter.

Suitable salt ion membranes may be more permeable to olefins than to paraffins. When a first side of the salt ion membrane is contacted with a mixed feed stream and a first aqueous salt stream, at least a portion of the one or more olefins from the mixed feed stream may migrate across the salt ion membrane to a second side of the salt ion membrane and the one or more paraffins may be substantially retained upon the first side of the salt ion membrane. Therefore, the first side of the salt ion membrane may be referred to herein as the "retentate side" of the salt ion membrane, and the second side of the salt ion membrane may be referred to as the "permeate side" of the salt ion membrane.

Suitable salt ion membranes may include "fixed site" or "supported liquid" types, each of which may comprise a copper (I) salt, a silver (I) salt, or any combination thereof to facilitate transport of at least one olefin from the retentate side of the salt ion membrane to the permeate side of the salt ion membrane.

U.S. Patent Application Publication US 2018/0001277 and U.S. Pat. No. 10,258,929 describe suitable salt ion membranes comprising a carboxylic acid-functionalized polyimide, in which the carboxylic acid functional groups are ion-exchanged or chelated with metal cations such as silver (I) or copper (I) cations. The salt ion membranes may comprise a relatively porous, thin, dense skin layer fabricated from a polyimide, a blend of two or more different polyimides or a blend of a polyimide and a polyethersulfone, and a relatively porous, thin, dense skin layer of comprising a hydrophilic polymer such as chitosan or sodium alginate, a metal salt (e.g., silver nitrate) or a mixture of a metal salt (e.g., silver nitrate) and hydrogen peroxide.

U.S. Patent Application Publication 2017/0354918 describes suitable salt ion membranes comprising a relatively hydrophilic, nanoporous support membrane, a hydrophilic polymer inside the pores of the nanoporous support membrane, a thin, nonporous, hydrophilic polymer layer coated on the surface of the support membrane, and one or more metal salts incorporated in the hydrophilic polymer on the surface of the support membrane and in the hydrophilic polymer inside the pores of the nanoporous support membrane. The average pore diameter of the nanoporous support membrane may be about 10 nm or less. The hydrophilic polymer comprising the support membrane may include polymers such as, for example, polyethersulfone (PES), a blend of polyethersulfone and polyimide, cellulose acetate, cellulose triacetate, and a blend of cellulose acetate and cellulose triacetate. The hydrophilic polymer within the pores may include polymers such as, for example, chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The nanoporous support membrane can be either an asymmetric integrally skinned membrane or a thin film composite membrane with either flat sheet (spiral wound) or hollow fiber geometry. Again, metal salts such as Cu (I), Ag (I), or any combination thereof may be present in the membrane.

U.S. Pat. No. 10,569,233 describes suitable salt ion membranes comprising a nanoporous polyethersulfone/polyvinylpyrrolidone blend support membrane, a hydrophilic polymer inside nanopores of the support membrane, a hydrophilic polymer coating layer on a surface of the support membrane and metal salts in the hydrophilic polymer coating layer and in the hydrophilic polymer inside the nanopores of the support membrane. Again, metal salts such as Cu (I), Ag (I), or any combination thereof may be present in the membrane.

U.S. Pat. No. 7,361,800 describes suitable salt ion membranes comprising a polysaccharide having Ag (I), Cu (I), or any combination thereof bound thereto. Examples of suitable polysaccharides may include natural polysaccharides such as alginic acid, pectic acid, chondroitin, hyaluronic acid and xanthan gum; cellulose, chitin, pullulan, derivatives such as $C_{1-6}$ esters, ethers and alkylcarboxy derivatives thereof and phosphates of these natural polysaccharides such as partially methyl esterified alginic acid, carbomethoxylated alginic acid, phosphorylated alginic acid and aminated alginic acid; salts of anionic cellulose derivatives such as carboxymethyl cellulose, cellulose sulfate, cellulose phosphate, sulfoethyl cellulose and phosphonoethyl cellulose; and semi-synthetic polysaccharides such as guar gum phosphate and chitin phosphate. Specific examples of suitable polysaccharides include those composed of salts of chitosan and its derivatives such as N-acylated chitosan, chitosan phosphate and carbomethoxylated chitosan. The salt ion membranes may also include blends of a polysaccharide as a majority component (e.g., at least about 60 wt % based on total mass) and one or more other polymers as a minority component (e.g., up to about 40 wt %), such as, for example, polyvinyl alcohol (PVA), neutral polysaccharides such as starch and pullulan, and grafted ionized polysaccharides obtained by grafting a hydrophilic vinyl monomer such as acrylic acid.

U.S. Pat. No. 9,782,724 describes a suitable supported liquid salt ion membrane. In the case of a supported liquid salt ion membrane, the first aqueous salt stream may serve as a replenishment liquid for maintaining membrane performance. The membrane may similarly comprise natural or functionalized polysaccharides, such as chitosan, as discussed above. Metal salts such as Cu (I), Ag (I), or any combination thereof may be present in the supported liquid within the salt ion membrane.

U.S. Patent Application Publication 2018/0111099 describes suitable salt ion membranes incorporating fluorinated silver ionomers as a membrane material. The ionomers may contain pendant sulfonic acid groups.

The salt ion membrane may be maintained under conditions similar to those at which the mixed feed stream and the first aqueous salt stream are supplied thereto. Thus, the salt ion membrane may be maintained at a temperature of about 5° C. to about 80° ° C., or from about 20° ° C. to about 70° C., or from about 40° C. to about 65° C., and at a pressure of about 2 bar to about 40 bar, or about 5 bar to about 30 bar, or about 8 bar to about 25 bar.

A pressure drop occurs as at least a portion of the one or more olefins pass through the salt ion membrane from the retentate side to the permeate side. That is, the permeate side may have a lower olefin partial pressure than does the retentate side of the salt ion membrane. The pressure drop may range from about 0.2 to about 2 bar, or about 0.5 bar to about 1.5 bar. Alternately, the pressure drop may be at least about 1.5 bar. The olefin partial pressure on the permeate side of the salt ion membrane may range from about 1 bar to about 10 bar, and a correspondingly higher pressure may be present on the retentate side.

The olefin-rich permeate stream and the olefin-lean retentate stream may both be obtained under conditions similar to those associated with the mixed feed stream, the first aqueous salt stream, and the salt ion membrane. Thus, olefin-rich permeate stream and the olefin-lean retentate stream may be independently obtained at a temperature of about 5° C. to about 80° C., or from about 20° ° C. to about 70° C., or from about 40° ° C. to about 65° C., and at a pressure of about 2 bar to about 40 bar, or about 5 bar to about 30 bar, or about 8 bar to about 25 bar. Salt ion membrane aqueous salt phase may be obtained with at least one of the olefin-rich permeate stream or the olefin-lean retentate stream.

A concentration of olefins in the olefin-rich permeate stream may be at least about 90 wt %, or at least about 95 wt %, or at least about 99 wt %, or at least about 99.5 wt %, or at least about 99.9 wt %, based on total hydrocarbons in the olefin-rich permeate stream and excluding any water (from the salt ion membrane aqueous salt phase). Non-olefin components from the mixed feed stream may constitute the balance of total hydrocarbons in the olefin-rich permeate stream. At least about 90 wt %, or at least about 95 wt %, or at least about 99 wt %, or at least about 99.5 wt %, or at least about 99.9 wt % of the one or more olefins in the mixed feed stream may be extracted into the olefin-rich permeate stream, based on total olefins in the mixed feed stream.

A concentration of olefins in the olefin-lean retentate stream may range from about 1 wt % to about 90 wt %, or about 5 wt % to about 80 wt %, or about 10 wt % to about 70 wt %, or about 10 wt % to about 50 wt %, based on total hydrocarbons in the olefin-lean retentate stream and excluding any water (from the salt ion membrane aqueous salt phase). Non-olefin components from the mixed feed stream may constitute the balance of total hydrocarbons in the olefin-rich permeate stream.

The second aqueous salt stream may have a lower olefin concentration than does the first aqueous salt stream (unless both the first and second aqueous salt streams comprise substantially no olefins). In non-limiting examples, the first and second aqueous salt streams may both comprise substantially no olefins if both streams are supplied from a fresh aqueous salt solution, such as to provide makeup volume. More typically, at least one of, and preferably both of, the first and second aqueous salt streams comprise at least some olefins, provided that the second aqueous salt stream comprises a lower olefin concentration. The first and second aqueous salt streams may be obtained by recycling salt ion membrane aqueous salt phase, optionally with further conditioning thereof, as discussed in further detail hereinafter. Process configurations suitable for recycling the salt ion membrane aqueous salt phase are discussed in more detail hereinafter. Fresh aqueous salt solution or water may also be supplied as a makeup stream in combination with recycled salt ion membrane aqueous salt phase provided as the first and/or second aqueous salt stream, such as to increase the volume for either of these streams.

Provided that the second aqueous salt stream is obtained from the salt ion membrane aqueous salt phase, the olefin concentration in the second aqueous salt stream may range from about 0.1 mol % to about 20 mol %, provided that the first aqueous salt stream has a higher olefin concentration. In more specific examples, the olefin concentration in the second aqueous salt stream may range from about 0.5 mol % to about 10 mol %, or about 0.5 mol % to about 5 mol % or about 0.5 mol % to about 2 mol %. The olefin concentration of the second aqueous salt stream may be further adjusted to best support operation of a particular absorption device, examples of which are discussed further below, and an amount of olefins extracted within the absorption device and/or the rigor needed when performing a conditioning operation to achieve a particular olefin concentration in at least a portion of the second aqueous salt stream. It may be desirable to balance obtaining a concentration of olefins in the second aqueous salt stream that is as low as possible (to support good extraction within the absorption device) while maintaining the cost of conditioning at a reasonable level. For example, extensive heating during conditioning to achieve an olefin concentration that is as low as possible may provide unacceptable process economics, when less extensive heating may afford an acceptable (but not lowest possible) olefin concentration but at a more reasonable cost. Additional details concerning conditioning are provided further below.

Illustrative disclosure regarding extraction of olefins using a suitable metal salt and absorption device may be found in U.S. Pat. Nos. 4,174,353 and 6,395,952, each of which is incorporated herein by reference in its entirety. Suitable absorption devices may include any construct capable of contacting two liquid phases with one another to promote extraction of at least one component from a first liquid into a second liquid. Examples of suitable absorption devices may include, for example, an absorption column (tower), a rotating packed bed contactor, and a compact contacting unit. By way of non-limiting example, suitable rotating packed bed contactors are described in further detail in U.S. Pat. No. 4,283,255, which is incorporated herein by reference in its entirety. By way of further non-limiting example, suitable compact contacting units are described in U.S. Pat. No. 8,899,557, which is also incorporated herein by reference in its entirety. Unless otherwise specified, the absorption device may be operated under temperature and pressure conditions similar to those of the salt ion membrane.

An olefin-rich aqueous salt stream and an olefin-lean hydrocarbon stream may be obtained from the absorption device. Thus, the olefin-rich aqueous salt stream and the olefin-lean hydrocarbon stream may both be obtained under conditions similar to those associated with the mixed feed stream, the first aqueous salt stream, and the salt ion membrane. Accordingly, olefin-rich aqueous salt stream and the olefin-lean hydrocarbon stream may be independently obtained at a temperature of about 5° C. to about 80° C., or from about 20° C. to about 70° C., or from about 40° C. to about 65° C., and at a pressure of about 2 bar to about 40 bar, or about 5 bar to about 30 bar, or about 8 bar to about 25 bar.

The olefin-rich aqueous salt stream may comprise at least about 5 wt % of the at least one olefin present in the olefin-lean retentate stream introduced to the absorption device. In other examples, the olefin-rich aqueous salt stream may comprise at least about 20 wt %, or at least about 50 wt %, or at least about 90 wt %, or at least about 99 wt % of the at least one olefin present in the olefin-lean retentate stream. Various factors may influence the amount of olefins present in the olefin-rich aqueous salt stream obtained from the absorption device such as, for example, the concentration of the at least one olefin in the mixed feed stream, and the amount of olefins removed from the mixed feed stream as the olefin-rich permeate stream.

Once obtained from the absorption device, the olefin-rich aqueous salt stream may be returned to the salt ion membrane as at least a portion of the first aqueous salt stream to promote further separation of at least one olefin and at least one paraffin from the mixed feed stream.

Optionally, at least a portion of the mixed feed stream may be introduced directly to the absorption device. In instances where a portion of the mixed feed stream is introduced directly to the absorption device, the olefin-rich aqueous salt stream may comprise at least about 5 wt %, or at least about 20 wt %, or at least about 50 wt %, or at least about 90 wt %, or at least about 99 wt % of the at least one olefin present in the olefin-lean retentate stream and the portion of the mixed feed stream introduced directly to the absorption device.

The olefin concentration in the olefin-lean hydrocarbon stream is lower than the olefin concentration in the olefin-lean retentate stream introduced to the absorption device and/or an olefin concentration combined in the olefin-lean retentate stream and mixed feed stream introduced to the absorption device. The olefin-lean hydrocarbon stream may comprise about 20 wt % or less olefins, or about 10 wt % or less olefins, or about 5 wt % or less olefins, or about 2 wt % or less olefins, or about 1 wt % or less olefins, or about 0.5 wt % or less olefins, each based on total mass of the olefin-lean hydrocarbon stream. Preferably, the olefin-lean hydrocarbon stream may be substantially olefin-free.

Further, the olefin-lean hydrocarbon stream obtained from the absorption device may comprise at least a majority of the one or more paraffins present in the mixed feed stream. In non-limiting examples, the olefin-lean hydrocarbon stream may comprise at least about 75 wt % of the paraffins in the mixed feed stream, or at least about 80 wt %, or at least about 85 wt %, or at least about 90 wt %, or at least about 95 wt %, or at least about 99 wt %, each based upon total mass of paraffins in the mixed feed stream. Other hydrocarbons and/or impurities within the mixed feed stream may also be removed within the olefin-lean hydrocarbon stream obtained from the absorption device.

In discussing additional aspects of the foregoing in further detail, the processes of the present disclosure will be described in reference to the FIGS.

Figure 1B:
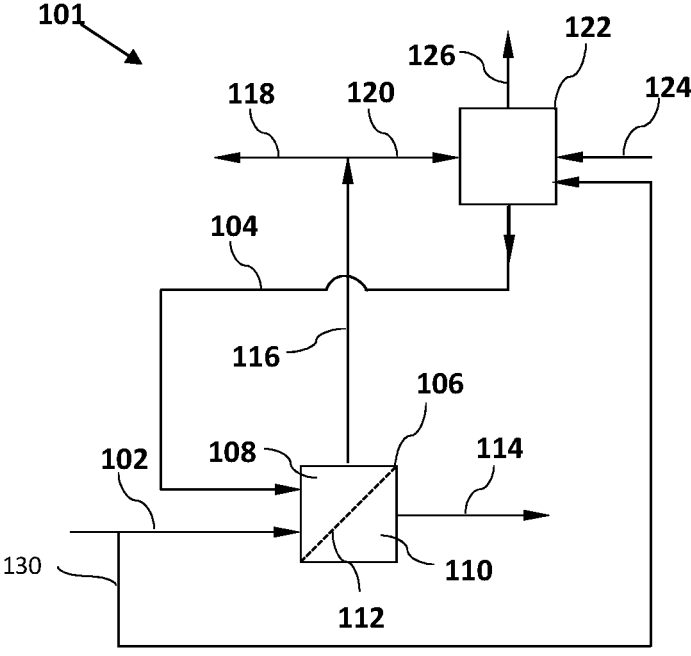

FIGS. 1A and 1B are block diagrams showing an olefin separation process of the present disclosure, in which a second aqueous salt stream is externally supplied. As shown in FIG. 1A, process 100 provides a mixed feed stream comprising at least one olefin and at least one paraffin in line 102 and a first aqueous salt stream in line 104, each of which are introduced to and contact salt ion membrane 106. Within salt ion membrane 106 there resides feed-receiving zone 108 that appropriately distributes the mixed feed stream and the first aqueous salt stream in multi-phase flow over a feed-side surface of membrane material 112. Multi-phase flow may be established with appropriate consideration of the composition and conditions of the mixed feed stream in line 102 and the first aqueous salt stream in line 104 when mixed, either within salt ion membrane 106 as shown in FIG. 1A, or optionally prior to entering salt ion membrane 106. The multiple phases may comprise at least a hydrocarbon phase containing olefins and an aqueous salt phase. The hydrocarbon phase may be a vapor, or a liquid that is at least partially immiscible in the aqueous salt phase. Alternately, there may be both a vapor hydrocarbon phase and a liquid hydrocarbon phase, each containing olefins and that is at least partially immiscible in the aqueous salt phase. In some embodiments, there may be multiple liquid hydrocarbon phase that are at least partially immiscible in each other and in the aqueous salt phase, optionally in further combination with a vapor hydrocarbon phase containing olefins.

At least a portion of the olefins in the mixed feed stream, along with a small fraction of paraffins within feed-receiving zone 108, move through membrane material 112 to permeate-receiving zone 110. The olefins passing through membrane material 112 are then removed from salt ion membrane 106 as an olefin-rich permeate stream in line 114. The olefin-rich permeate stream may be further purified (not shown), if desired. The olefin-rich permeate stream obtained from permeate-receiving zone 110 and removed in line 114 may comprise at least a hydrocarbon-rich phase containing at least a portion of the one or more olefins from the mixed feed stream. The hydrocarbon-rich phase within the olefin-rich permeate stream may be vapor, liquid, or any combination thereof.

Optionally, the olefin-rich permeate stream may further comprise at least a portion of a salt ion membrane liquid aqueous salt phase contacted with salt ion membrane 106. The location where the salt ion membrane aqueous salt phase is obtained may depend upon the specific type of salt ion membrane employed, the specific components, phases and the conditions that are present within permeate-receiving zone 110, particularly the pressure within permeate-receiving zone 110. For example, certain types of salt ion membrane 106 may allow co-permeation of some aqueous salt phase through membrane material 112. In various embodiments, the olefin-rich permeate stream within permeate-receiving zone 110 and removed in line 114 may be a hydrocarbon-rich vapor phase containing olefins and a salt ion membrane aqueous salt phase, or the olefin-rich permeate stream may be a hydrocarbon-rich liquid phase containing olefins and a salt ion membrane aqueous salt phase in which the hydrocarbon-liquid rich liquid phase is at least partially immiscible. In another embodiment, the olefin-rich permeate stream may include a hydrocarbon-rich vapor phase containing olefins, a hydrocarbon-rich liquid phase containing olefins, and a salt ion membrane aqueous salt phase in which the hydrocarbon-rich liquid phase containing olefins is at least partially immiscible with the other phases. More specific examples of processes in which the olefin-rich permeate stream also contains salt ion membrane aqueous salt phase are discussed in reference to the further FIGS. below.

In accordance with the foregoing, the quantity of olefins in the mixed feed stream is decreased. The residual mixed feed stream and the first aqueous salt stream remaining in feed-receiving zone 108 may still contain at least a portion of the one or more olefins originally provided with the mixed feed stream, and a mixture of the residual mixed feed stream and the first aqueous salt stream may exit salt ion membrane 106 as an olefin-lean retentate stream in line 116. The olefin-lean retentate stream in line 116 may comprise at least a hydrocarbon-lean phase containing at least some olefins that may be vapor, liquid, or any combination thereof, or may contain two immiscible hydrocarbon liquid phases, optionally in combination with a vapor phase. In process 100, the olefin-lean retentate stream in line 116 further includes at least a portion of a salt ion membrane liquid aqueous salt phase contacted with salt ion membrane 106, which may represent at least a majority of the salt ion membrane aqueous salt phase or substantially all of the salt ion membrane aqueous salt phase.

The olefin-lean retentate stream in line 116 is the further directed to absorption device 122 via line 120. Optionally, before entering line 120, the olefin-lean retentate stream may be split into two portions, with a first portion of the olefin-lean retentate stream being provided to absorption device 122 via line 120 and a second portion of the olefin-lean retentate stream being diverted away from absorption device 122 as a purge stream or product stream in line 118. Components within the purge stream or product stream obtained from line 118 may be further processed, if desired.

A second aqueous salt stream in line 124 is also provided to absorption device 122 along with the portion of the olefin-lean retentate stream in line 120. The second aqueous salt stream may have a lower olefin concentration than does the first aqueous salt stream. As shown, the second aqueous salt stream is provided in line 124 without being recycled from another source, such as from a separate reservoir of aqueous salt solution. In other embodiments, the second aqueous salt stream may comprise at least a portion of the salt ion membrane aqueous salt phase, as discussed herein-below in reference to subsequent FIGS. That is, the salt ion membrane aqueous salt phase may be recycled and provided to line 124 as at least a portion of the second aqueous salt stream, either from olefin-rich permeate stream (further recycling details shown in FIGS. 2-5) or olefin-lean retentate stream (further recycling details shown in FIGS. 7-9). Optionally, recycled salt ion membrane aqueous salt phase provided as the second aqueous salt stream may be further supplemented by an aqueous salt solution or water provided from an external source, such as within a makeup stream, if a larger volume of second aqueous salt solution is needed to promote effective contacting within absorption device 122.

Within absorption device 122, the portion of the olefin-lean retentate stream is contacted with the second aqueous salt stream under conditions effective to produce an olefin-rich aqueous salt stream containing at least a portion of the one or more olefins from the olefin-lean retentate stream. The olefin-rich aqueous salt stream exits absorption device 122 in line 104, and an olefin-lean hydrocarbon product stream comprising at least a portion of the one or more paraffins from the olefin-lean retentate stream is removed from absorption device 122 via line 126. Establishing suitable conditions in absorption device 122 for producing the olefin-rich aqueous salt stream may include correlating the composition, flowrate, pressure and temperature of the second liquid aqueous salt stream in line 124 with those same properties of the portion of the olefin-lean retentate stream in line 120. Additional conditions that may be considered include, for example, the geometry of absorption device 122 and the temperature and pressure within absorption device 122. Operation of absorption device 122 may be conducted in vapor-liquid, liquid-liquid or vapor-liquid-liquid mode as dictated by application-specific requirements, primarily based on the phase characteristics of the portion of the olefin-lean retentate stream provided in line 120.

After exiting absorption device 122, the olefin-rich aqueous salt stream in line 104 may be returned to salt ion membrane 106 for further olefin separation to take place therefrom. The olefin-rich aqueous salt stream also provides a source for the first aqueous salt stream provided to salt ion membrane 106. Although not shown in FIG. 1A, it is to be appreciated that additional first aqueous salt stream may be provided from an external source of aqueous salt solution or water added as a makeup stream. As shown in FIG. 1A, the olefin-rich aqueous salt stream is returned to salt ion membrane 106 separately from the mixed feed stream in line 102. It is to be appreciated, however, that the olefin-rich aqueous salt stream and the mixed feed stream may be combined with one another, if desired, prior to being returned to salt ion membrane 106. Such process configurations are provided herein and discussed further below.

Processes of the present disclosure may further comprise introducing at least a second portion of the mixed feed stream to the absorption device. Such diversion of a mixed feed stream to an absorption device is shown in FIG. 1B. Process 101 of FIG. 1B is substantially similar to process 100 of FIG. 1A, except a portion of the mixed feed stream in line 102 may be diverted to absorption device 122 via bypass line 130. Olefins within the mixed feed stream introduced to absorption device 122 may similarly be extracted into an olefin-rich aqueous salt stream that is subsequently removed via line 104 and provided to salt ion membrane 106 in accordance with the disclosure above. It may become advantageous to divert at least a portion of the mixed feed stream to absorption device 122 as the olefin concentration therein decreases, such as about 50 wt % or below, or about 35 wt % or below, or about 20 wt % or below, based on total mass of the mixed feed stream. Other elements of FIG. 1B are substantially similar to those described above in reference to FIG. 1A and are not described again in detail in the interest of brevity. Even if not expressly depicted in subsequent FIGS., it is to be appreciated that a bypass line similar to bypass line 130 may be incorporated in any of the process configurations described or depicted herein.

In some embodiments, the olefin-rich permeate stream may further comprise at least a portion of the salt ion membrane aqueous salt phase, and at least a portion of the second aqueous salt stream may be obtained from the salt ion membrane aqueous salt phase comprising the olefin-rich permeate stream. The salt ion membrane aqueous salt phase provided as at least a portion of the second aqueous salt stream may be conditioned in various manners before being provided as at least a portion of the second aqueous salt stream, as discussed hereinbelow in reference to FIGS. 2-5. That is, FIGS. 2-5 are block diagrams showing various configurations of olefin separation processes of the present disclosure, in which at least a portion of the second aqueous salt stream is provided from a permeate side of the salt ion membrane.

In some embodiments, the olefin-lean retentate stream may further comprise at least a portion of the salt ion membrane aqueous salt phase, and at least a portion of the second aqueous salt stream may be obtained from the salt ion membrane aqueous salt phase comprising the olefin-lean retentate stream. The salt ion membrane aqueous salt phase provided as at least a portion of the second aqueous salt stream may be conditioned in various manners before being provided as at least a portion of the second aqueous salt stream, as discussed hereinbelow with reference to FIGS.

6A-9. That is, FIGS. 6A-9 are block diagrams showing various process configurations of olefin separation processes of the present disclosure, in which at least a portion of the second aqueous salt stream is provided from a retentate side of the salt ion membrane.

Figure 2:
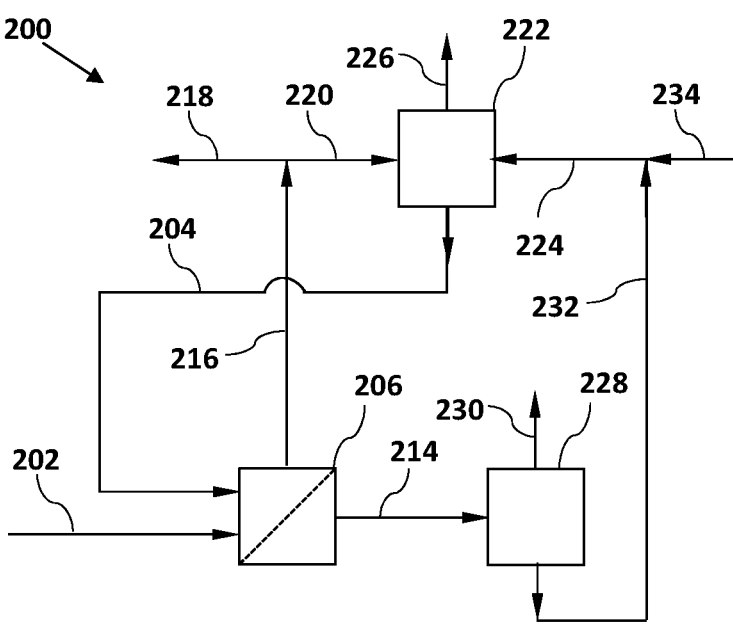
FIGS. 2-5 are block diagrams showing various configurations of olefin separation processes of the present disclosure, in which at least a portion of a second aqueous salt stream is provided from a permeate side of a salt ion membrane.

FIG. 2 is a block diagram showing an olefin separation process of the present disclosure, in which a salt ion membrane aqueous salt phase associated with the olefin-rich permeate stream is conditioned and supplied as at least a portion of the second aqueous salt stream. In process 200 of FIG. 2, a mixed feed stream in line 202 and a first aqueous salt stream in line 204 are introduced to salt ion membrane 206, which may be similar in structure and function to salt ion membrane 106 (FIG. 1), under conditions effective to form at least two phases within salt ion membrane 206. Salt ion membrane 206 produces an olefin-rich permeate stream in line 214 and an olefin-lean retentate stream in line 216. The olefin-rich permeate stream in line 214 may comprise both a hydrocarbon-rich phase containing one or more olefins from the mixed feed stream and salt ion membrane aqueous salt phase, and the olefin-lean retentate stream in line 216 may comprise both a hydrocarbon-lean phase containing one or more olefins from the mixed feed stream and salt ion membrane aqueous salt phase. One or both of the olefin-rich permeate stream and the olefin-lean retentate stream may comprise a vapor phase in particular process configurations.

The olefin-rich permeate stream in line 214 is subjected to conditioning operation 228 comprising at least one of changing pressure, changing temperature, and separating phases to produce conditioned salt ion membrane aqueous salt phase in line 232, which is olefin-lean relative to the salt ion membrane aqueous salt phase in the olefin-rich permeate stream. Conditioning operation 228 may be conducted such that a lower olefin concentration in the salt ion membrane aqueous salt phase at least temporarily results. The conditioned salt ion membrane aqueous salt phase in line 232 is supplied as at least a portion of the second aqueous salt solution provided to absorption device 222, as discussed further below, and has a lower olefin concentration than that of the first aqueous salt stream in line 204. Conditioning operation 228 also produces a conditioned hydrocarbon-rich stream in line 230 that may be withdrawn as product. The conditioned hydrocarbon-rich stream may be olefin-rich relative to the mixed feed stream. Conditioning operation 228 thus may produce at least two phases, typically at least a hydrocarbon phase containing olefins and a liquid phase that is a conditioned salt ion membrane aqueous salt phase. In one embodiment, the hydrocarbon phase containing olefins may be a vapor, or the hydrocarbon phase containing olefins may be a liquid that is at least partially immiscible in the conditioned salt ion membrane aqueous salt phase. In another embodiment, there may be both a vapor hydrocarbon phase containing olefins and a liquid hydrocarbon phase containing olefins that is at least partially immiscible in the conditioned salt ion membrane aqueous salt phase. In other embodiments, there may be multiple liquid hydrocarbon phases containing olefins that are at least partially immiscible in each other and in the conditioned salt ion membrane aqueous salt phase, potentially in further combination with a vapor hydrocarbon phase containing olefins.

The olefin-lean retentate stream in line 216 is optionally split into two streams, with a portion of both a hydrocarbon-lean phase containing olefins, preferably a vapor phase, and the salt ion membrane aqueous salt phase in line 220 being directed to absorption device 222. The balance of the olefin-lean retentate stream in line 216 is removed from process 200 in line 218, either as a purge stream or as product stream for further processing, for example.

A second aqueous salt stream in line 224 is also provided to absorption device 222. The second aqueous salt stream in line 224 may comprise the conditioned salt ion membrane aqueous salt phase in line 232 and optionally further include a makeup stream comprising an aqueous salt solution or water supplied in line 234. Any ratio of conditioned salt ion membrane aqueous salt phase and makeup stream may be introduced to absorption device 222. The makeup stream in line 234 serves to replace water and salt removed from process 200, for example, purposefully with the balance of the olefin-lean retentate stream exiting process 200 in line 218, and residual water that is removed with the conditioned hydrocarbon-rich stream comprising one or more olefins in line 230 and an olefin-lean hydrocarbon stream comprising one or more paraffins removed from process 200 in line 226.

Within absorption device 222, the introduced portion of the olefin-lean retentate stream is contacted with the second aqueous salt stream under conditions effective to promote olefin extraction into the second aqueous salt stream, thereby producing an olefin-rich aqueous salt stream that contains at least a portion of at least one olefin from the olefin-lean retentate stream. The olefin-rich aqueous salt stream exits absorption device 222 and becomes the first aqueous salt stream that is provided to salt ion membrane 206 via line 204. Also obtained from absorption device 222 is an olefin-lean hydrocarbon stream comprising at least a portion of the one or more paraffins from the olefin-lean product stream, which is removed from process 200 via line 226.

Figure 3:
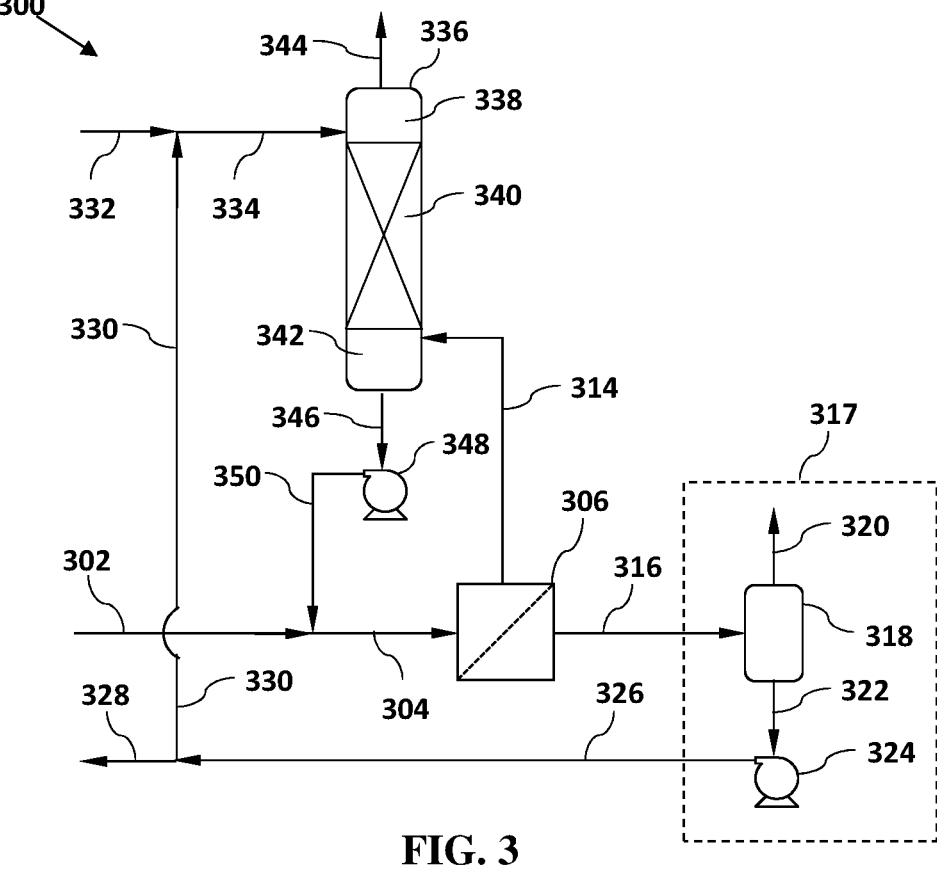

FIG. 3 is a block diagram showing an olefin separation process of the present disclosure, in which a salt ion membrane aqueous salt phase associated with the olefin-rich permeate stream is conditioned through phase separation and then supplied as at least a portion of the second aqueous salt stream. In process 300 of FIG. 3, a mixed feed stream in line 302 and a first aqueous salt stream in line 350 are mixed under conditions effective to form at least two phases in line 304, and the at least two phases are provided as a multi-phase flow to salt ion membrane 306. Although shown as being mixed in line 304, the mixed feed stream and the first aqueous salt stream may be introduced separately to salt ion membrane 306 under conditions to establish multi-phase flow as well. As previously described, salt ion membrane 306 may provide an olefin-rich permeate stream in line 316 and an olefin-lean retentate stream in line 314. In process 300, the olefin-rich permeate stream in line 316 may comprise both a hydrocarbon-rich phase containing at least a portion of the one or more olefins from the mixed feed stream and a salt ion membrane aqueous salt phase. The hydrocarbon-rich phase within the olefin-rich permeate stream may be vapor, liquid, or any combination thereof, preferably a vapor phase containing at least one olefin, in combination with the salt ion membrane aqueous salt phase. The olefin-lean retentate stream in line 314 may comprise at least a hydrocarbon-lean phase containing at least some olefins that may be vapor, liquid, or any combination thereof, or may contain two immiscible hydrocarbon liquid phases, optionally in combination with a vapor phase. Preferably, the olefin-lean retentate stream in line 314 comprises both a hydrocarbon-lean vapor phase containing olefins and a salt ion membrane aqueous salt phase.

The olefin-rich permeate stream in line 316 is provided to conditioning operation 317, which includes a phase separation with flash drum 318 and a pressure increase with first liquid pump 324. More specifically, the olefin-rich permeate stream in line 316 is provided to flash drum 318 to promote phase separation and create a conditioned hydrocarbon-rich stream comprising one or more olefins in line 320 that is removed from process 300 as a product stream, and a conditioned salt ion membrane aqueous salt phase that is olefin-lean in line 322. The conditioned salt ion membrane aqueous salt phase in line 322 has a lower concentration of olefins than the first aqueous salt stream in line 350. The lower concentration of olefins in the conditioned salt ion membrane aqueous salt phase may be obtained in view of the phase equilibrium of this system with an appropriate reduction of the olefin partial pressure of the olefin-rich permeate stream in line 316.

The conditioned salt ion membrane aqueous salt phase in line 322 is further provided to first liquid pump 324 to produce a pressurized, conditioned salt ion membrane aqueous salt phase in line 326. The applied pressure is sufficient to move the pressurized conditioned salt ion membrane aqueous salt phase to absorption device 336.

Before reaching absorption device 336, the pressurized, conditioned salt ion membrane aqueous salt phase in line 326 is optionally split into two streams. A small portion of the pressurized, conditioned salt ion membrane aqueous salt phase may be removed from process 300 as an aqueous salt purge stream in line 328. The aqueous salt purge stream may facilitate removal of one or more contaminants that may be introduced to process 300 with the mixed feed stream. Contaminants may react with a metal salt comprising the first or second aqueous salt streams, typically the salt's cation constituent, to form one or more species that is ineffective for absorbing olefins, thus reducing the efficacy of the first and second aqueous salt streams circulating in process 300. For example, acetylene, methylacetylene or hydrogen sulfide contaminants present in the mixed feed stream in line 302 may react with silver ions to form silver acetylides or silver sulfate that are ineffective for absorbing olefins. Such unwanted species may be removed with the aqueous salt purge stream in line 328. The aqueous salt purge stream may be discarded or, for example, be sent to a separate facility to reclaim the metal salt or a contaminant-reacted form thereof.

The balance of the pressurized, conditioned salt ion membrane aqueous salt phase in line 326 is taken into line 330, and introduced to absorption device 336 as a portion of the second aqueous salt stream in line 334. A makeup stream comprising an aqueous salt solution or water in line 332 may further introduce at least a portion of the second aqueous salt stream via line 334, wherein the makeup stream is mixed in line 334 with the balance of the pressurized, conditioned salt ion membrane aqueous salt phase from line 330. The makeup stream in line 332 serves to replace the water and salt removed from process 300 purposefully in the aqueous salt purge stream in line 328, and the water that is removed within the conditioned hydrocarbon-rich stream comprising one or more olefins in line 320 and olefin-lean hydrocarbon stream comprising at least a portion of the one or more paraffins from the mixed feed stream due to the phase equilibrium of these systems. In alternative embodiments, water and salt may be replaced by introducing such a makeup stream to other locations within process 300, and further may be introduced separately to convenient locations as distinct aqueous salt or water streams.

At least a portion of, and preferably the entirety of, the olefin-lean retentate stream in line 314 comprising a hydrocarbon-lean phase containing at least one olefin, preferably a vapor phase, and a salt ion membrane aqueous salt phase is directed to absorption device 336 along with the second aqueous salt stream in line 334. In process 300, absorption device 336 is shown as a conventional absorption column, within which the hydrocarbon-lean phase containing the at least one olefin and the second aqueous salt stream are contacted under conditions effective to produce an olefin-lean hydrocarbon product stream comprising one or more paraffins in line 344, and an olefin-rich aqueous salt stream in line 346 that contains at least a portion of the one or more olefins from the mixed feed stream. In the absorption column, the force of gravity enables countercurrent contacting of the lower density hydrocarbon phase(s), as vapor and/or liquid, as the hydrocarbon phase(s) rise up the absorption column and the higher density aqueous salt stream falls down the absorption column. Hence, the higher density second aqueous salt stream in line 334 is shown as entering near or proximal to the top of the absorption column, such as within absorber top settling zone 338, and the lower density olefin-lean retentate stream in line 314 is shown as entering near or proximal to the bottom of the absorption column, such as within absorber bottom settling zone 342. Any location at which the olefin-lean retentate stream enters an absorption column below the second aqueous salt stream may be satisfactory, however. Absorber top settling zone 338 may be an open volume that serves to substantially reduce an amount of the higher density aqueous salt solution that may be entrained in the lower density hydrocarbon phase(s) as it exits the absorption column as the olefin-lean hydrocarbon product stream in line 344. To that end, particularly when the lower density hydrocarbon phase is a vapor, certain internals known to the skilled practitioner may be placed in absorber top settling zone 338 to minimize the amount of higher density second aqueous salt stream in the olefin-lean hydrocarbon product stream in line 344, such as a de-mister screen. Similarly, absorber bottom settling zone 342 may be an open volume that serves to substantially reduce the amount of the lower density hydrocarbon phase(s) that may be entrained in the olefin-rich aqueous salt stream as it exits the absorption column via line 346. The mass transfer efficiency and stagewise absorption performance of such contacting may be enhanced by including column mixing internals zone 340 within the absorption column, such as perforated trays or packing elements familiar to persons having ordinary skill in the art. Internals zone 340 is located in between absorber top settling zone 338 and absorber bottom settling zone 342.

At least a portion of, and preferably all of, the olefin-rich aqueous salt stream that contains at least a portion of the one or more olefins is provided to second liquid pump 348 via line 346. Second liquid pump 348 increases the pressure of the olefin-rich aqueous salt stream in line 346, such pressure being sufficient to provide the olefin-rich aqueous salt stream as at least a portion of the first aqueous salt stream in line 350 that is provided to salt ion membrane 306.

Figure 4:
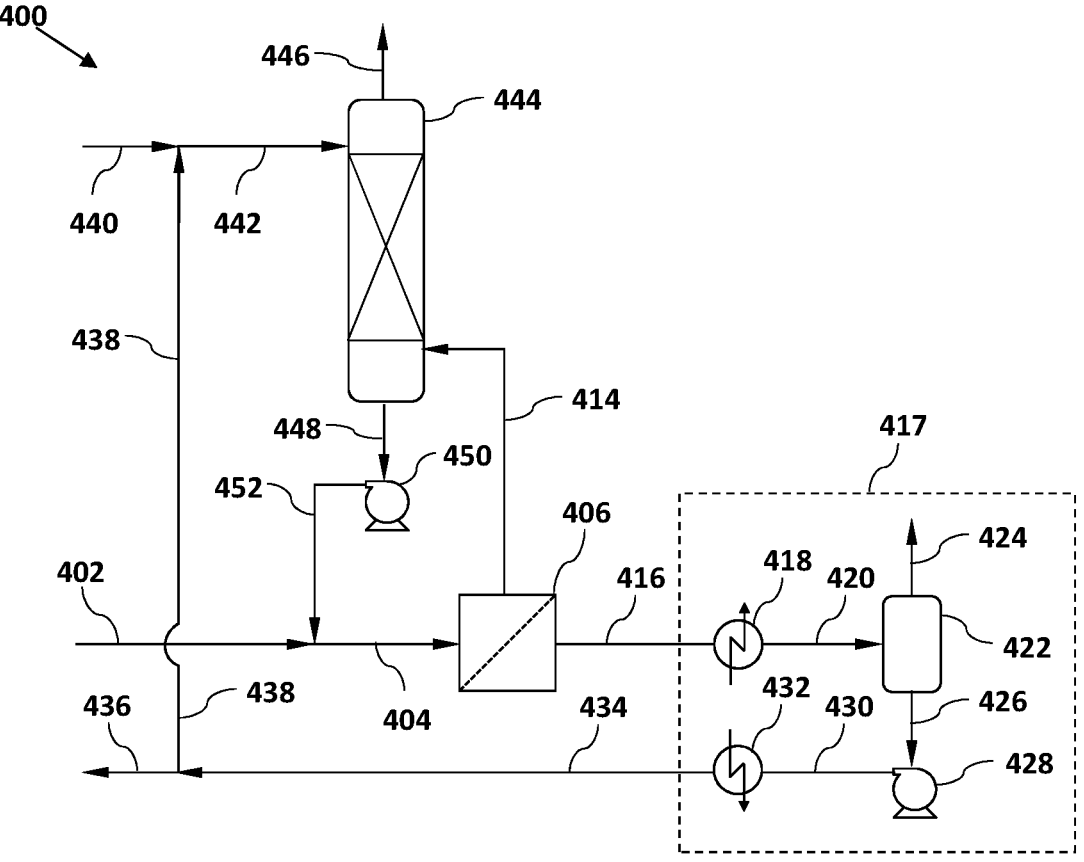

FIG. 4 is a block diagram showing an olefin separation process of the present disclosure, in which a salt ion membrane aqueous salt phase associated with the olefin-rich permeate stream is conditioned through both phase separation and a temperature change and then supplied as at least a portion of the second aqueous salt stream. In process 400 of FIG. 4, a mixed feed stream in line 402 and a first aqueous salt stream in line 452 are mixed under conditions effective to form at least two phases in line 404, and the at least two phases are provided as a multi-phase flow to salt ion membrane 406. Although shown as being mixed in line 404, the mixed feed stream and the first aqueous salt stream may be introduced separately to salt ion membrane 406 under conditions to establish multi-phase flow as well. As previously described, salt ion membrane 406 may provide an olefin-rich permeate stream in line 416 and an olefin-lean retentate stream in line 414. In process 400, the olefin-rich permeate stream in line 416 may comprise both a hydrocarbon-rich phase containing at least a portion of the one or more olefins from the mixed feed stream and a salt ion membrane aqueous salt phase. The hydrocarbon-rich phase within the olefin-rich permeate stream may be vapor, liquid, or any combination thereof, preferably a vapor phase containing at least one olefin in combination with the salt ion membrane aqueous salt phase. The olefin-lean retentate stream in line 414 may comprise at least a hydrocarbon-lean phase containing at least some olefins that may be vapor, liquid, or any combination thereof, or may contain two immiscible hydrocarbon liquid phases, optionally in combination with a vapor phase. Preferably, the olefin-lean retentate stream in line 414 comprises both a hydrocarbon-lean vapor phase containing olefins and a salt ion membrane aqueous salt phase.

The olefin-rich permeate stream in line 416 is provided to conditioning operation 417, which includes a temperature increase with first heat exchanger 418, a phase separation with flash drum 422, a pressure increase with first liquid pump 428, and a temperature decrease with second heat exchanger 432. More specifically, the olefin-rich permeate stream in line 416 is provided to first heat exchanger 418 to increase the temperature of the olefin-rich permeate stream and provide a heated olefin-rich permeate stream in line 420. The heated olefin-rich permeate stream is then provided to flash drum 422 to promote phase separation and create a conditioned hydrocarbon-rich stream comprising one or more olefins in line 424 that is removed from process 400 as a product stream, and a conditioned salt ion membrane aqueous salt phase that is olefin-lean in line 426. The conditioned salt ion membrane aqueous salt phase in line 426 has a lower concentration of olefins than the first aqueous salt stream in line 452. The lower concentration of olefins in the conditioned salt ion membrane aqueous salt phase may be obtained in view of the phase equilibrium of this system. As a result of heating and flashing, one or more olefins are transferred from the salt ion membrane aqueous salt phase into the conditioned hydrocarbon-rich stream exiting process 400 in line 426.

The conditioned salt ion membrane aqueous salt phase in line 426 is further provided to first liquid pump 428 to produce a pressurized, conditioned salt ion membrane aqueous salt phase in line 430. The applied pressure is sufficient to move the pressurized conditioned salt ion membrane aqueous salt phase to absorption device 444 after passing through second heat exchanger 432. Second heat exchanger 432 decreases the temperature of the conditioned salt ion membrane aqueous salt phase and provides a further conditioned salt ion membrane aqueous salt phase in line 434. The cooling operation, by virtue of the phase equilibrium of the system, increases the capacity of the further conditioned salt ion membrane aqueous salt phase to absorb one or more olefins upon being introduced to absorption device 444.

Before reaching absorption device 444, the further conditioned salt ion membrane aqueous salt phase in line 434 is optionally split into two streams. A small portion of the further conditioned salt ion membrane aqueous salt phase may be removed from process 400 as an aqueous salt purge stream in line 436. The aqueous salt purge stream may facilitate removal of one or more contaminants, as previously described above for process 300. The balance of the further conditioned salt ion membrane aqueous salt phase in line 434 is taken into line 438, and introduced to absorption device 444 as a portion of the second aqueous salt stream in line 442. A makeup stream in line 440 may further introduce at least a portion of the second aqueous salt stream via line 442, wherein the makeup stream is mixed in line 442 with the balance of the further conditioned salt ion membrane aqueous salt phase in line 438. The makeup stream may be introduced at alternative locations and for the purposes discussed above in reference to process 300.

At least a portion of, and preferably the entirety of, the olefin-lean retentate stream in line 414 comprising a hydrocarbon-lean phase containing olefins, preferably a vapor phase, and a salt ion membrane aqueous salt phase is directed to absorption device 444 along with the second aqueous salt stream in line 442. In process 400, absorption device 444 is shown as a conventional absorption column, within which the hydrocarbon-lean phase containing olefins and the second aqueous salt stream are contacted under conditions effective to produce an olefin-lean hydrocarbon product stream comprising one or more paraffins in line 446, and an olefin-rich aqueous salt stream in line 448 that contains at least a portion of the one or more olefins from the mixed feed stream. The absorption column comprising absorption device 444 may have similar features to that described above for process 300.

At least a portion of, and preferably all of, the olefin-rich aqueous salt stream that contains at least a portion of the one or more olefins is provided to second liquid pump 450 via line 448. Second liquid pump 450 increases the pressure of the olefin-rich aqueous salt stream in line 448, such pressure being sufficient to provide the olefin-rich aqueous salt stream as at least a portion of the first aqueous salt stream in line 452 that is provided to salt ion membrane 406.

Figure 5:
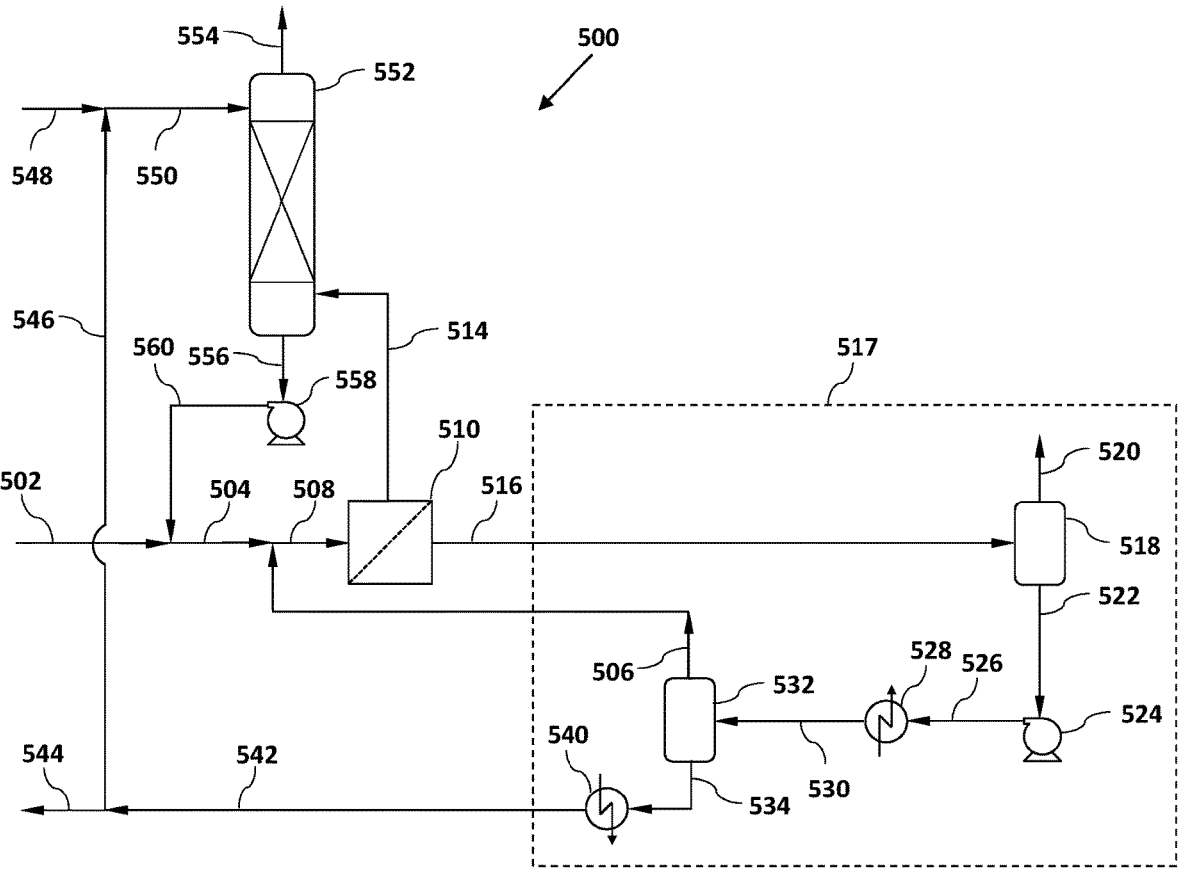

FIG. 5 is a block diagram showing an olefin separation process of the present disclosure, in which a salt ion membrane aqueous salt phase associated with the olefin-rich permeate stream is conditioned through two phase separations and a temperature change and then supplied as at least a portion of the second aqueous salt stream. In process 500 of FIG. 5, a mixed feed stream in line 502 and a first aqueous salt stream in line 560 are combined in line 504 and are subsequently transferred to line 508, wherein there are conditions effective to form at least two phases. The at least two phases in line 508 are provided as a multi-phase flow to salt ion membrane 510. A conditioned hydrocarbon-rich stream comprising one or more olefins is further introduced to line 508 via line 506, as discussed further hereinafter, for reintroduction to salt ion membrane 510. Although shown as being combined in line 504 and forming phases in line 508, the mixed feed stream, the first aqueous salt stream, and the conditioned hydrocarbon-rich stream comprising one or more olefins may be introduced separately to salt ion membrane 510 under alternative conditions to establish multiphase flow as well. As previously described, salt ion membrane 510 may provide an olefin-rich permeate stream in line 516 and an olefin-lean retentate stream in line 514. In process 500, the olefin-rich permeate stream in line 516 may comprise both a hydrocarbon-rich phase containing at least a portion of the one or more olefins from the mixed feed stream and a salt ion membrane aqueous salt phase. The hydrocarbon-rich phase within the olefin-rich permeate stream may be vapor, liquid, or any combination thereof, preferably a vapor phase containing at least one olefin in combination with the salt ion membrane aqueous salt phase. The olefin-lean retentate stream in line 514 may comprise at least a hydrocarbon-lean phase containing at least some olefins that may be vapor, liquid, or any combination thereof, or may contain two immiscible hydrocarbon liquid phases, optionally in combination with a vapor phase. Preferably, the olefin-lean retentate stream in line 514 comprises both a hydrocarbon-lean vapor phase containing olefins and a salt ion membrane aqueous salt phase.

The olefin-rich permeate stream in line 516 is provided to conditioning operation 517, which includes a first phase separation with first flash drum 518, a pressure increase with first liquid pump 524, a temperature increase with first heat exchanger 528, a second phase separation with second flash drum 532, and a temperature decrease with second heat exchanger 540. More specifically, the olefin-rich permeate stream in line 516 is provided to first flash drum 518 to promote phase separation and create a conditioned hydrocarbon-rich stream comprising one or more olefins in line 520 that is removed from process 500 as a product stream, and a conditioned salt ion membrane aqueous salt phase that is olefin-lean in line 522. The conditioned salt ion membrane aqueous salt phase in line 522 is further provided to first liquid pump 524 to produce a pressurized, conditioned salt ion membrane aqueous salt phase in line 526. The applied pressure is sufficient to move the pressurized, conditioned salt ion membrane aqueous salt phase elsewhere in process 500, including to at least absorption device 552. The pressurized, conditioned salt ion membrane aqueous salt phase in line 526 is passed through first heat exchanger 528 to increase the temperature of the pressurized, conditioned salt ion membrane aqueous salt phase, which then enters line 530 as heated and pressurized, conditioned salt ion membrane aqueous salt phase. The heated and pressurized, conditioned salt ion membrane aqueous salt phase is then provided to second flash drum 532 to form a conditioned hydrocarbon-rich stream comprising one or more olefins in line 506, and a heated, conditioned salt ion membrane aqueous salt phase in line 534. The conditioned hydrocarbon-rich stream in line 506 constitutes a majority of the remaining olefins that are not removed from the olefin-rich permeate stream in first flash drum 518. The olefins in the conditioned hydrocarbon-rich stream in line 506 are recycled to salt ion membrane 510 after forming two or more phases in line 508. For reasons similar to those discussed above, the heated, conditioned salt ion membrane aqueous salt phase in line 534 has a lower concentration of olefins than does the first aqueous salt stream in line 560. The heated, conditioned salt ion membrane aqueous salt phase in line 534 is then provided to second heat exchanger 540 to form a further conditioned salt ion membrane aqueous salt phase, which promotes a temperature decrease of the salt ion membrane aqueous salt phase within line 542 to increase its olefin absorption capacity once introduced to absorption device 552.

Before reaching absorption device 552, the further conditioned salt ion membrane aqueous salt phase in line 542 is optionally split into two streams. A small portion of the further conditioned salt ion membrane aqueous salt phase may be removed from process 500 as an aqueous salt purge stream in line 544. The aqueous salt purge stream may facilitate removal of one or more contaminants, as previously described above for process 300. The balance of the further conditioned salt ion membrane aqueous salt phase in line 542 is taken into line 546, and introduced to absorption device 552 as a portion of the second aqueous salt stream in line 550. A makeup stream in line 548 may further introduce at least a portion of the second aqueous salt stream via line 550, wherein the makeup stream is mixed in line 550 with the balance of the conditioned salt ion membrane aqueous salt phase in line 546. The makeup stream may be introduced at alternative locations and for the purposes discussed above in reference to process 300.

At least a portion of, and preferably the entirety of, the olefin-lean retentate stream in line 514 comprising a hydrocarbon-lean phase containing olefins, preferably a vapor phase, and a salt ion membrane aqueous salt phase is directed to absorption device 552 along with the second aqueous salt stream in line 550. In process 500, absorption device 552 is shown as a conventional absorption column, within which the hydrocarbon-lean phase containing olefins and the second aqueous salt stream are contacted under conditions effective to produce an olefin-lean hydrocarbon stream comprising one or more paraffins in line 554, and an olefin-rich aqueous salt stream in line 556 that contains at least a portion of the one or more olefins from the mixed feed. The absorption column comprising absorption device 552 may have similar features to that described above for process 300.

At least a portion of, and preferably all of, the olefin-rich aqueous salt stream that contains at least a portion of the one or more olefins is provided to second liquid pump 558 via line 556. Second liquid pump 558 increases the pressure of the olefin-rich aqueous salt stream in line 556, such pressure being sufficient to provide the olefin-rich aqueous salt stream as at least a portion of the first aqueous salt stream in line 560 that is provided to salt ion membrane 510.

Figure 6A:
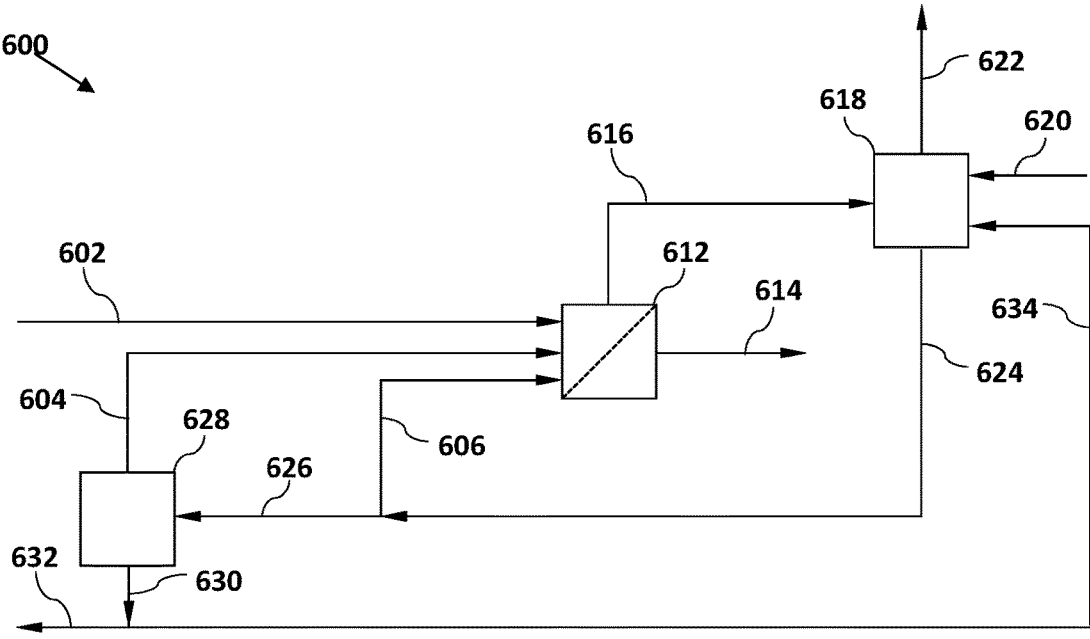
FIGS. 6A-9 are block diagrams showing various process configurations of olefin separation processes of the present disclosure, in which at least a portion of a second aqueous salt stream is provided from a retentate side of a salt ion membrane.
Figure 6B:
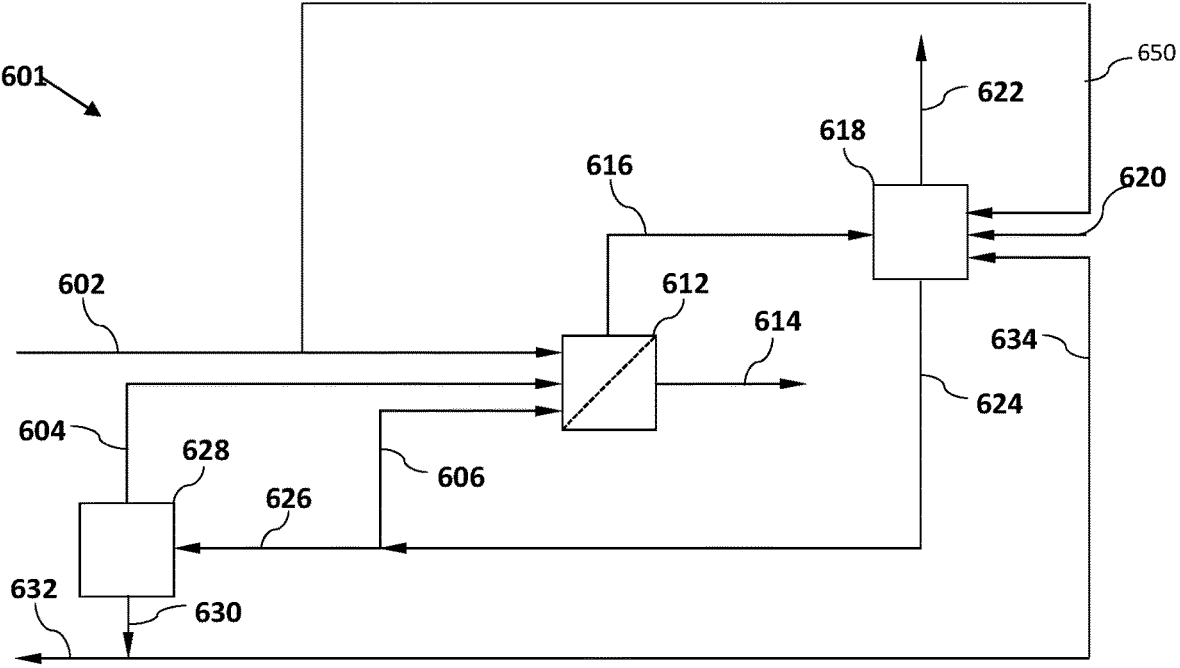

FIGS. 6A and 6B are block diagrams showing an olefin separation process of the present disclosure, in which a second aqueous salt stream is at least partially supplied from an olefin-lean retentate stream. In process 600 of FIG. 6A, a mixed feed stream comprising at least one olefin and at least one paraffin is supplied in line 602 and a first aqueous salt stream in line 606 are provided to salt ion membrane 612 under conditions effective to form at least two phases therein. Although shown as being introduced to salt ion membrane 612 separately, it is to be appreciated that the mixed feed stream and the first aqueous salt stream may be premixed in a line before entering salt ion membrane 612, including forming at least two phases therein. In addition to the one or more olefins in the mixed feed stream, a conditioned hydrocarbon-rich stream comprising one or more olefins is obtained via recycling and supplied to salt ion membrane 612 via line 604, as discussed hereinafter. Salt ion membrane 612 produces an olefin-rich permeate stream in line 614 and an olefin-lean retentate stream in line 616. The olefin-rich permeate stream in line 614 comprises a hydrocarbon-rich phase containing olefins and may optionally further comprise a salt ion membrane aqueous salt phase, and the olefin-lean retentate stream in line 616 comprises both a hydrocarbon-lean phase, which may be a vapor phase containing olefins, and a salt ion membrane aqueous salt phase. In this case, the olefin-rich permeate stream in line 614 is withdrawn as a product stream from process 600, optionally with further purification thereafter (not shown), if desired.

At least a portion of, and preferably the entirety of the olefin-lean retentate stream in line 616 is directed to absorption device 618, along with a second aqueous salt stream in line 634. Makeup stream in line 620 comprising water or an aqueous salt may be supplied to absorption device 618 for the reasons discussed above in reference to process 300. Within absorption device 618, the olefin-lean retentate stream is contacted with the second aqueous salt stream and optionally the makeup stream under conditions effective to produce an olefin-rich aqueous salt stream in line 624 that contains at least a portion of the one or more olefins from the mixed feed stream, and an olefin-lean hydrocarbon product stream comprising one or more paraffins in line 622 that is removed from process 600.

At least a portion of the olefin-rich aqueous salt stream in line 624 may be returned to salt ion membrane 612 via line 606 as at least a portion of the first aqueous salt stream. The balance of the olefin-rich aqueous salt stream in line 624 is provided to conditioning operation 628. Conditioning operation 628 produces a conditioned salt ion membrane aqueous salt phase in, which has a lower olefin concentration than that of the first aqueous salt stream in line 606. The conditioned salt ion membrane aqueous salt phase may be split into two streams, with a small portion being removed from process 600 as an aqueous salt solution purge stream in line 632 for the reasons discussed above in reference to process 300. The balance of the conditioned salt ion membrane aqueous salt phase in line 630 is taken into line 634 and introduced to absorption device 618 as at least a portion of the second aqueous salt stream. Conditioning operation 628 also produces a conditioned hydrocarbon-rich stream comprising one or more olefins that is provided to salt ion membrane 612 by line 604.

Process 601 of FIG. 6B is substantially similar to process 600 of FIG. 6A, except a portion of the mixed feed stream in line 602 may be diverted to absorption device 618 via bypass line 650. Olefins within the mixed feed stream introduced to absorption device 618 via bypass line 650 may similarly be extracted into an olefin-rich aqueous salt stream that is subsequently removed via line 624 and provided to salt ion membrane 612 and/or conditioning operation 628 in accordance with the disclosure above. It may become advantageous to divert at least a portion of the mixed feed stream as the olefin concentration therein decreases, such as about 50 wt % or below, or about 35 wt % or below, or about 20 wt % or below, based on total mass of the mixed feed stream. Other elements of FIG. 6B are substantially similar to those described above in reference to FIG. 6A and are not described again in detail in the interest of brevity. Again, it is to be emphasized that even if not expressly depicted in subsequent FIGS., it is to be appreciated that a bypass line similar to bypass line 650 may be incorporated in any of the process configurations described or depicted herein.

Figure 7:
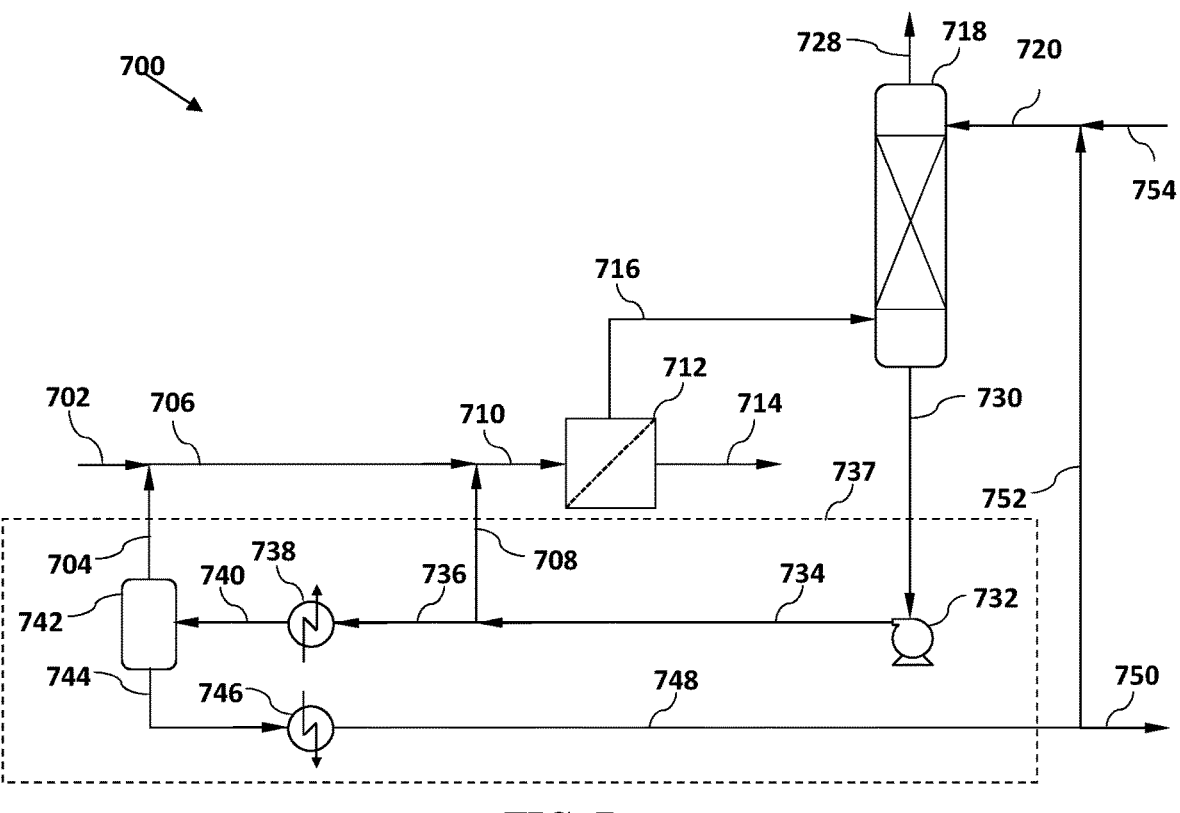

FIG. 7 is a block diagram showing an olefin separation process of the present disclosure, in which a salt ion membrane aqueous salt phase associated with the olefin-lean retentate stream is conditioned through phase separation and two temperature changes and then supplied as at least a portion of the second aqueous salt stream. In process 700 of FIG. 7, a mixed feed stream in line 702 and a first aqueous salt stream in line 708 are provided to salt ion membrane 712 under conditions effective to form at least two phases therein after being combined as a mixture in line 710. Although shown as being introduced to salt ion membrane 712 as a mixture in line 710, it is to be appreciated that the mixed feed stream and the first aqueous salt stream may be introduced to salt ion membrane 712 separately under conditions effective to form at least two phases therein under multiphase flow conditions. In addition, a conditioned hydrocarbon-rich stream comprising one or more olefins is obtained via conditioning and supplied to salt ion membrane 712 via lines 704, 706, and 710, as discussed hereinafter. It is likewise to be appreciated that the conditioned hydrocarbon-rich stream comprising one or more olefins may be introduced directly to salt ion membrane 712 without first being mixed with other phases in the manner discussed hereinbelow. Salt ion membrane 712 produces an olefin-rich permeate stream in line 714 and an olefin-lean retentate stream in line 716. The olefin-rich permeate stream in line 714 comprises a hydrocarbon-rich phase containing olefins and may optionally further comprise a salt ion membrane aqueous salt phase, and the olefin-lean retentate stream in line 716 comprises both a hydrocarbon-lean phase, which may be a vapor phase containing olefins, and a salt ion membrane aqueous salt phase. In this case, the olefin-rich permeate stream in line 714 is withdrawn as a product stream from process 700, optionally with further purification thereafter (not shown), if desired.

At least a portion of, and preferably the entirety of the olefin-lean retentate stream in line 716 is directed to absorption device 718, along with a second aqueous salt stream in line 720. In process 700, absorption device 718 is shown as a conventional absorption column, within which the olefin-lean retentate stream containing olefins and the second aqueous salt stream are contacted under conditions effective to produce an olefin-lean hydrocarbon stream comprising one or more paraffins in line 728, and an olefin-rich aqueous salt stream in line 730 that contains at least a portion of the one or more olefins from the mixed feed stream. The olefin-rich aqueous salt stream in line 730 comprises at least a portion of the salt ion membrane aqueous salt phase obtained from the olefin-lean retentate stream provided to absorption device 718.

At least a portion of, and preferably the entirety of the olefin-rich aqueous salt stream in line 730 is provided to conditioning operation 737, which includes a pressure increase with liquid pump 732, a temperature increase with first heat exchanger 738, a phase separation in flash drum 742, and a temperature decrease in second heat exchanger 746. More specifically, the olefin-rich aqueous salt stream in line 730 is provided to liquid pump 732 to increase the pressure and form a pressurized, olefin-rich aqueous salt stream in line 734. The applied pressure is sufficient to move the pressurized, olefin-rich aqueous salt phase elsewhere in process 700, including to at least absorption device 718. A portion of the pressurized, olefin-rich aqueous salt stream in line 734 is provided as the first aqueous salt stream in line 708, and the balance of the pressurized, olefin-rich aqueous salt stream in line 734 is taken in line 736 and sent to first heat exchanger 738. First heat exchanger 738 increases the temperature of the pressurized, olefin-rich aqueous salt stream in line 736 to create a pressurized and heated olefin-rich aqueous salt stream in line 740. The pressurized and heated olefin-rich aqueous salt stream in line 740 is sent to flash drum 742 to produce a conditioned olefin-rich hydrocarbon phase in line 704 that may be combined with the mixed feed stream in line 706 and subsequently supplied to salt ion membrane 712. Flash drum 742 also produces a conditioned salt ion membrane aqueous salt phase that is olefin-lean in line 744. The conditioned salt ion membrane aqueous salt phase in line 744 has a lower concentration of olefins than does the first aqueous salt stream in line 708 by virtue of the heating and flashing operation, which transfers olefins from the pressurized and heated olefin-rich aqueous salt stream in line 740 to the conditioned olefin-rich hydrocarbon phase that is recycled in line 704.

The conditioned salt ion membrane aqueous salt phase in line 744 is directed to second heat exchanger 746 to reduce the temperature of the conditioned salt ion membrane aqueous salt phase and generate a cooled, conditioned salt ion membrane aqueous salt phase that is olefin-lean in line 748. Cooling, by virtue of the phase equilibria of these systems, increases the efficacy of the cooled, conditioned salt ion membrane aqueous salt phase in line 748 to absorb one or more olefins upon its eventual introduction to absorption device 718. The cooled, conditioned salt ion membrane aqueous salt phase in line 748 is optionally split into two streams, with a small portion being removed from process 700 as an aqueous salt purge stream in line 750 for the purposes discussed above in reference to process 300. The balance of the cooled, conditioned salt ion membrane aqueous salt phase in line 748 is taken into line 752 and introduced to absorption device 718 as at least a portion of the second aqueous salt stream in line 720. The second aqueous salt stream in line 720 may further includes a makeup stream from line 754, again for the purposes considered above in regard to process 300.

Figure 8:
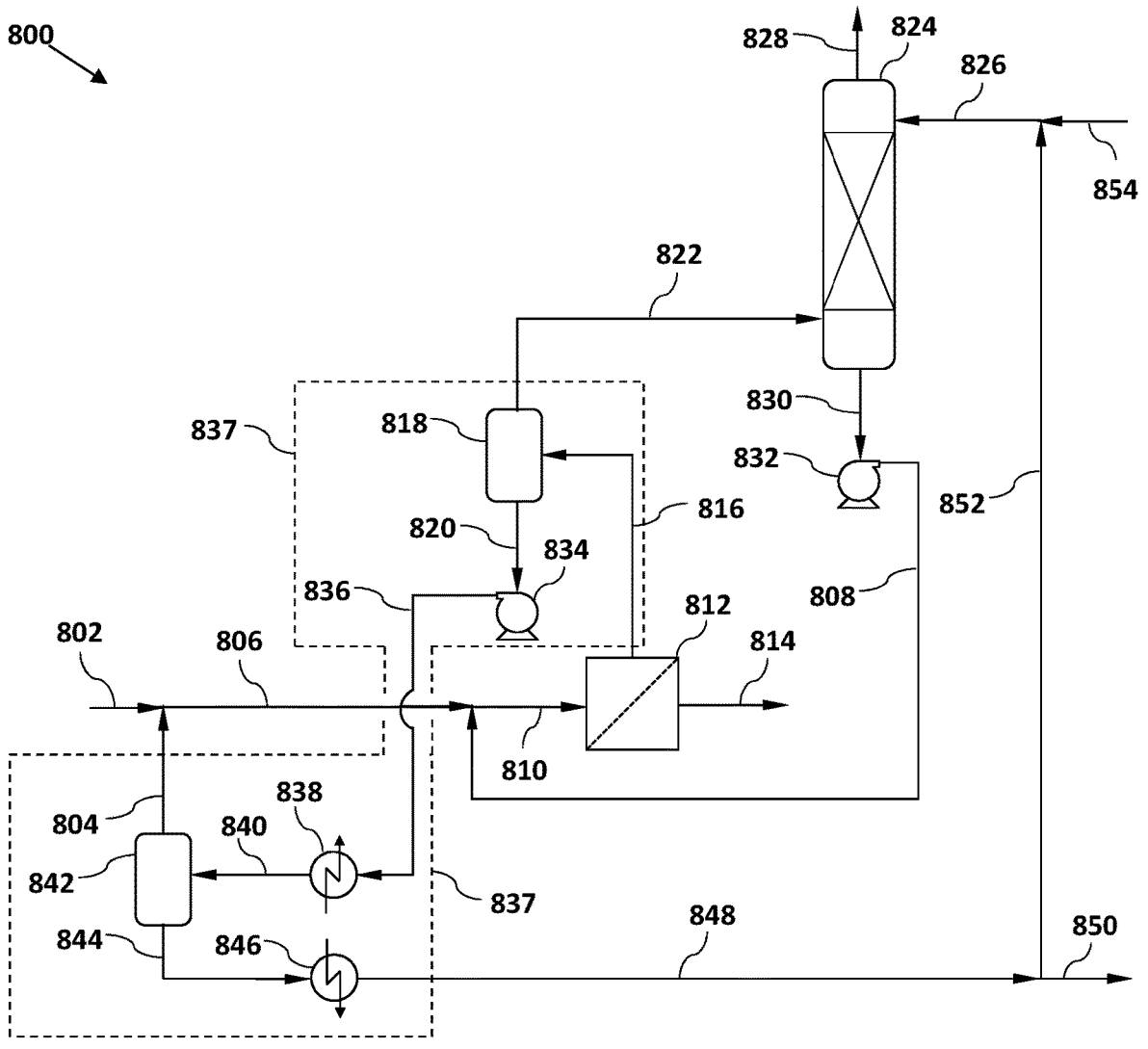

FIG. 8 is a block diagram showing an olefin separation process of the present disclosure, in which the olefin-lean retentate stream is conditioned through phase separation before being supplied to the absorption device. In process 800 of FIG. 8, a mixed feed stream in line 802 and a first aqueous salt stream in line 808 are provided to salt ion membrane 812 under conditions effective to form at least two phases therein after being combined as a mixture in line 810. Although shown as being introduced to salt ion membrane 812 as a mixture in line 810, it is to be appreciated that the mixed feed stream and the first aqueous salt stream may be introduced to salt ion membrane 812 separately under conditions effective to form at least two phases therein under multi-phase flow conditions. A conditioned olefin-rich hydrocarbon phase comprising at least one olefin in line 804 is further provided to salt ion membrane 812 after being combined with the mixed feed stream in line 806. Salt ion membrane 812 produces an olefin-rich permeate stream in line 814 and an olefin-lean retentate stream in line 816. The olefin-rich permeate stream in line 814 comprises a hydrocarbon-rich phase containing olefins and may optionally further comprise a salt ion membrane aqueous salt phase, and the olefin-lean retentate stream in line 816 comprises both a hydrocarbon-lean phase, which may be a vapor phase containing olefins, and a salt ion membrane aqueous salt phase. In this case, the olefin-rich permeate stream in line 814 is withdrawn as a product stream from process 800, optionally with further purification thereafter (not shown), if desired.

At least a portion of, and preferably the entirety of the olefin-lean retentate stream in line 816 is directed to conditioning operation 837, which includes phase separation in first flash drum 818, a pressure increase with liquid pump 834, a temperature increase with first heat exchanger 838, phase separation in second flash drum 842, and a temperature decrease in second heat exchanger 846. More specifically, the olefin-lean retentate stream in line 816 is provided to first flash drum 818 to promote phase separation into an olefin-lean hydrocarbon-rich stream in line 822, which may be a vapor stream, and a conditioned salt ion membrane aqueous salt phase in line 820. The conditioned salt ion membrane aqueous salt phase in line 820 is provided to liquid pump 834 and pressurized to produce a pressurized, conditioned salt ion membrane aqueous salt phase in line 836. The applied pressure is sufficient to move the pressurized, olefin-rich aqueous salt phase elsewhere in process 800, including to at least absorption device 824. At least a portion of, and preferably all of the pressurized, salt ion membrane aqueous salt phase in line 836 is sent to first heat exchanger 838. First heat exchanger 838 increases the temperature of the pressurized, salt ion membrane aqueous salt phase in line 836 to create a pressurized and heated salt ion membrane aqueous salt phase in line 840. The pressurized and heated salt ion membrane aqueous salt phase in line 840 is sent to second flash drum 842 to produce a conditioned olefin-rich hydrocarbon phase in line 804 that may be combined with the mixed feed stream in line 806 and subsequently supplied to salt ion membrane 812. Second flash drum 842 also produces a conditioned salt ion membrane aqueous salt phase that is olefin-lean in line 844. The conditioned salt ion membrane aqueous salt phase in line 844 has a lower concentration of olefins than does the first aqueous salt stream in line 808 by virtue of the heating and flashing operation, which transfers olefins to the conditioned olefin-rich hydrocarbon phase that is recycled in line 804.

The conditioned salt ion membrane aqueous salt phase in line 844 is directed to second heat exchanger 846 to reduce the temperature of the conditioned salt ion membrane aqueous salt phase and generate a cooled, conditioned salt ion membrane aqueous salt phase that is olefin-lean in line 848. Cooling, by virtue of the phase equilibria of these systems, increases the efficacy of the cooled, conditioned salt ion membrane aqueous salt phase in line 848 to absorb one or more olefins upon its eventual introduction to absorption device 824. The cooled, conditioned salt ion membrane aqueous salt phase in line 848 is optionally split into two streams, with a small portion being removed from process 800 as an aqueous salt purge stream in line 850 for the purposes discussed above in reference to process 300. The balance of the cooled, conditioned salt ion membrane aqueous salt phase in line 848 is taken into line 852 and introduced to absorption device 824 as at least a portion of the second aqueous salt stream provided via line 826. The second aqueous salt stream in line 826 may further include a makeup stream from line 854, again for the purposes considered above in regard to process 300.

The second aqueous salt stream in line 826 and the olefin-lean hydrocarbon rich stream in line 822 are provided to absorption device 824. In process 800, absorption device 824 is shown as a conventional absorption column, within which the olefin-lean hydrocarbon rich stream containing olefins and the second aqueous salt stream are contacted under conditions effective to produce an olefin-lean hydrocarbon product stream comprising one or more paraffins in line 828, and an olefin-rich aqueous salt stream in line 830 that contains at least a portion of the one or more olefins from the mixed feed stream. The olefin-rich aqueous salt stream in line 830 comprises at least a portion of the salt ion membrane aqueous salt phase obtained from the olefin-lean retentate stream provided to absorption device 824. At least a portion of, or preferably all of the olefin-rich aqueous salt stream in line 830 is provided to second liquid pump 832 to increase the pressure sufficiently to move the olefin-rich aqueous salt stream to salt ion membrane 812.

Figure 9:
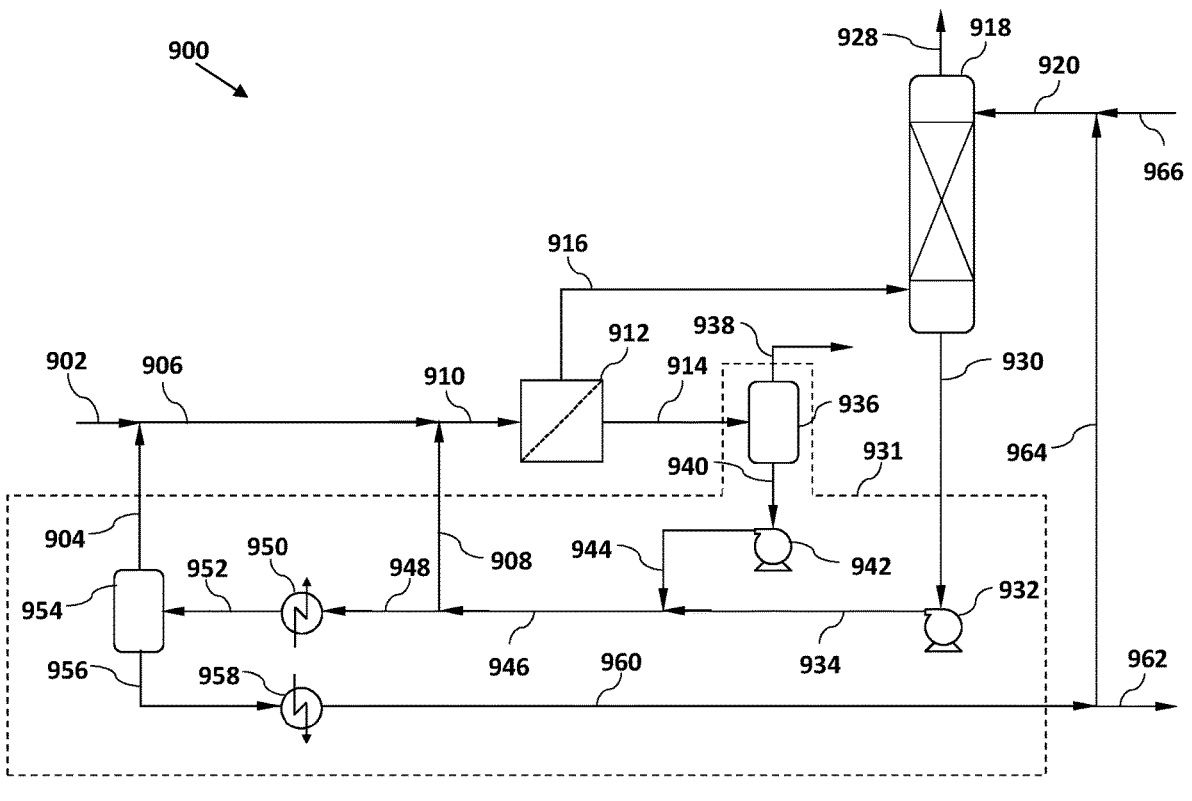

FIG. 9 is a block diagram showing an olefin separation process of the present disclosure, in which the olefin-rich permeate stream is conditioned before being supplied to the absorption device. In process 900 of FIG. 9, a mixed feed stream in line 902 and a first aqueous salt stream in line 908 are provided to salt ion membrane 912 under conditions effective to form at least two phases therein after being combined as a mixture in line 910. Although shown as being introduced to salt ion membrane 912 as a mixture in line 910, it is to be appreciated that the mixed feed stream and the first aqueous salt stream may be introduced to salt ion membrane 912 separately under conditions effective to form at least two phases therein under multi-phase flow conditions. A conditioned olefin-rich hydrocarbon phase comprising at least one olefin in line 904 is further provided to salt ion membrane 912 after being combined with the mixed feed stream in line 906. Salt ion membrane 912 produces an olefin-rich permeate stream in line 914 and an olefin-lean retentate stream in line 916. The olefin-rich permeate stream in line 914 comprises a hydrocarbon-rich phase containing olefins, preferably a vapor phase, and a salt ion membrane aqueous salt phase, and the olefin-lean retentate stream in line 916 comprises both a hydrocarbon-lean phase, which may be a vapor phase containing olefins, and a salt ion membrane aqueous salt phase.

At least a portion of, and preferably the entirety of the olefin-lean retentate stream in line 916 is directed to absorption device 918, along with second aqueous salt stream supplied in line 920. In process 900, absorption device 918 is shown as a conventional absorption column, within which the olefin-lean retentate stream containing olefins and the second aqueous salt stream are contacted under conditions effective to produce an olefin-lean hydrocarbon product stream comprising one or more paraffins in line 928, and an olefin-rich aqueous salt stream in line 930 that contains at least a portion of the one or more olefins from the mixed feed stream. The olefin-rich aqueous salt stream in line 930 comprises at least a portion of the salt ion membrane aqueous salt phase obtained from the olefin-lean retentate stream provided to absorption device 918.

At least a portion of, or preferably all of the olefin-rich aqueous salt stream in line 930 is provided to conditioning operation 931. Conditioning operation 931 includes a pressure increase with first liquid pump 932, a temperature increase with first heat exchanger 950, a phase separation with first flash drum 954, and a temperature decrease with second heat exchanger 958. The olefin-rich permeate stream in line 914 is also further conditioned in conditioning operation 931, wherein conditioning operation 931 further includes a phase separation with second flash drum 936 and a pressure increase with second liquid pump 942. More specifically, the olefin-rich aqueous salt stream in line 930 is provided to first liquid pump 932 to increase the pressure of the olefin-rich aqueous salt stream to create a pressurized olefin-rich aqueous salt stream in line 934. The pressure is sufficient to move the pressurized olefin-rich aqueous salt stream elsewhere in process 900, including to absorption device 918. The olefin-rich permeate stream in line 914 is also provided to second flash drum 936 to form an olefin-rich hydrocarbon product stream, preferably a vapor stream, comprising one or more olefins in line 938 that is removed from process 900, and a conditioned salt ion membrane aqueous salt phase in line 940. The conditioned salt ion membrane aqueous salt phase in line 940 is pressurized with second liquid pump 942, and the pressurized salt ion membrane aqueous salt phase in line 940 is combined in line 946 with the pressurized olefin-rich aqueous salt stream from line 934, thereby providing a mixed conditioned aqueous salt stream in line 946.

A portion of the mixed conditioned aqueous salt stream in line 946, which is olefin-lean, is introduced via line 908 as the first aqueous salt stream provided to salt ion membrane 912. The balance of the mixed conditioned aqueous salt stream in line 946 is taken in line 948 and provided to first heat exchanger 950 to create a heated, mixed conditioned aqueous salt stream in line 952. The heated, mixed conditioned aqueous salt stream in line 952 is subjected to phase separation in first flash drum 954 to produce a conditioned hydrocarbon-rich stream in line 904, which is provided to salt ion membrane 912 as described above, and a conditioned salt ion membrane aqueous salt phase in line 956. The conditioned salt ion membrane aqueous salt phase in line 956 has a lower concentration of olefins than does the first aqueous salt stream in line 908 by virtue of the heating and flashing operation, which transfers olefins to the conditioned hydrocarbon-rich stream that is recycled in line 904.

The conditioned salt ion membrane aqueous salt phase in line 956 is sent to second heat exchanger 958 to reduce its temperature and generate a cooled, conditioned salt ion membrane aqueous salt phase in line 960. Cooling, by virtue of the phase equilibria of these systems, increases the efficacy of the cooled, conditioned salt ion membrane aqueous salt phase in line 960 to absorb one or more olefins upon its eventual introduction to absorption device 918.

The cooled, conditioned salt ion membrane aqueous salt phase in line 960 is optionally split into two streams, with a small portion being removed from process 900 as an aqueous salt purge stream in line 962 for the purposes discussed above in reference to process 300. The balance of the cooled, conditioned salt ion membrane aqueous salt phase in line 960 is taken into line 964 and introduced to absorption device 918 as at least a portion of the second aqueous salt stream provided via line 920. The second aqueous salt stream in line 920 may further includes a makeup stream from line 966, again for the purposes considered above in regard to process 300.

It is to be appreciated that any embodiment herein employing an absorption column may alternately employ an alternative absorption device suitable for contacting a second aqueous salt stream and an olefin-lean retentate stream with one another. Process alternations commensurate with replacement of an absorption column with an alternative absorption device will be within the capabilities of one having ordinary skill in the art.

Embodiments disclosed herein include:

A. Processes for separating at least one olefin from at least one paraffin. The processes comprise: providing a mixed feed stream comprising at least one olefin and at least one paraffin; introducing at least a first portion of the mixed feed stream and a first aqueous salt stream to a salt ion membrane under conditions effective to form at least two phases while contacting the salt ion membrane; wherein the salt ion membrane is more permeable to olefins than to paraffins; obtaining an olefin-rich permeate stream and an olefin-lean retentate stream from the salt ion membrane, the olefin-lean retentate stream comprising at least a portion of the at least one olefin from the mixed feed stream; wherein at least one of the olefin-rich permeate stream and the olefin-lean retentate stream further comprises a salt ion membrane aqueous salt phase; introducing at least a portion of the olefin-lean retentate stream and a second aqueous salt stream to an absorption device under conditions effective to promote olefin extraction into the second aqueous salt stream; obtaining from the absorption device an olefin-rich aqueous salt stream comprising at least a portion of the at least one olefin from the olefin-lean retentate stream, and an olefin-lean hydrocarbon stream comprising at least a portion of the at least one paraffin from the mixed feed stream; and providing at least a portion of the olefin-rich aqueous salt stream as at least a portion of the first aqueous salt stream.

Embodiment A may have one or more of the following additional elements in any combination:

Element 1: wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream.

Element 2: wherein a makeup stream comprising an aqueous salt solution or water is supplied as at least a portion of the second aqueous salt stream.

Element 3: wherein the olefin-rich permeate stream further comprises at least a portion of the salt ion membrane aqueous salt phase, and at least a portion of the second aqueous salt stream is obtained from the salt ion membrane aqueous salt phase comprising the olefin-rich permeate stream.

Element 4: wherein the olefin-lean retentate stream comprises at least a portion of the salt ion membrane aqueous salt phase, and at least a portion of the second aqueous salt stream is obtained from the salt ion membrane aqueous salt phase comprising the olefin-lean retentate stream.

Element 5: wherein a first portion of the salt ion membrane aqueous salt phase is diverted away from a second portion of the salt ion membrane aqueous salt phase being provided to the absorption device.

Element 6: wherein the second aqueous salt stream has a lower olefin concentration than does the first aqueous salt stream.

Element 7: wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream, and wherein the process further comprises: performing a conditioning operation upon at least a portion of the salt ion membrane aqueous salt phase to produce the lower olefin concentration.

Element 8: wherein the conditioning operation comprises at least one action performed on the salt ion membrane aqueous salt phase selected from the group consisting of a temperature change, a pressure change, a phase separation, and any combination thereof.

Element 9: wherein the conditioning operation comprises at least phase separation of the salt ion membrane aqueous salt phase from a conditioned hydrocarbon-rich stream comprising one or more olefins.

Element 10: wherein the process further comprises introducing at least a portion of the conditioned hydrocarbon-rich stream to the salt ion membrane.

Element 11: wherein the salt ion membrane aqueous salt phase is separated from the conditioned hydrocarbon-rich stream as a hydrocarbon-lean stream, and at least a portion of the hydrocarbon-lean stream is provided to the absorption device as at least a portion of the second aqueous salt stream.

Element 12: wherein at least a portion of the hydrocarbon-lean stream is diverted away from the absorption device as a purge stream or a product stream.

Element 13: wherein the conditioning operation comprises changing a temperature of the salt ion membrane aqueous salt phase at least once.

Element 14: wherein changing the temperature of the salt ion membrane aqueous salt phase at least once comprises: raising the temperature of the salt ion membrane aqueous salt phase from a first temperature to a second temperature to lower an olefin absorption capacity thereof; after raising the temperature of the salt ion membrane aqueous salt phase to the second temperature, performing phase separation to separate the conditioned hydrocarbon-rich stream from the salt ion membrane aqueous salt phase; and after separating the conditioned hydrocarbon-rich stream from the salt ion membrane aqueous salt phase, lowering the temperature of the salt ion membrane aqueous salt phase from the second temperature to a third temperature to at least partially restore the olefin absorption capacity.

Element 15: wherein the first temperature and the third temperature are about equal.

Element 16: wherein the process further comprises performing a first phase separation prior to raising the temperature and separating a first conditioned hydrocarbon-rich stream comprising one or more olefins from the salt ion membrane aqueous salt phase.

Element 17: wherein the process further comprises performing phase separation upon the olefin-lean retentate stream and separating an olefin-lean hydrocarbon-rich stream from the salt ion membrane aqueous salt phase prior to raising the temperature of the salt ion membrane aqueous salt phase; and introducing at least a portion of the olefin-lean hydrocarbon rich stream to the absorption device.

Element 18: wherein the process further comprises raising pressure of the salt ion membrane aqueous salt phase prior to providing the salt ion membrane aqueous salt phase as at least a portion of the second aqueous salt stream.

Element 19: wherein at least a portion of the salt ion membrane aqueous salt phase is diverted away from the absorption device as a purge stream or a product stream.

Element 20: wherein the process further comprises introducing at least a second portion of the mixed feed stream to the absorption device.

Element 21: wherein the first and second aqueous salt streams comprise a silver (I) salt, a copper (I) salt, or any combination thereof.

Element 22: wherein the first and second aqueous salt streams comprise silver nitrate.

Element 23: wherein the salt ion membrane and the first and second aqueous salt streams each comprise one or more metal salts that are the same.

Element 24: wherein one or more olefins are obtained from the olefin-rich permeate stream at a purity of at least about 95 wt %, based on total hydrocarbons in the olefin-rich permeate stream.

Element 25: wherein the olefin-rich permeate stream contains at least about 95 wt % of the one or more olefins in the mixed feed stream, based on total olefins in the mixed feed stream.

Element 26: wherein an equal number of the salt ion membrane and the absorption device are present.

Element 27: wherein the olefin-rich permeate stream is obtained at a pressure of at least about 1.5 bar.

Element 28: wherein the absorption device is selected from the group consisting of an absorption column, a rotating packed bed, and a compact contacting unit.

Element 29: wherein the absorption device comprises an absorption column, the second aqueous salt stream is introduced to an upper portion of the absorption column and the at least a portion of the olefin-lean retentate stream is introduced to the absorption column below the second aqueous salt stream.

Element 30: wherein the absorption column comprises at least an absorber top settling zone, an absorber bottom settling zone, and an internals zone between the absorber top settling zone and the absorber bottom settling zone.

Element 31: wherein the at least a portion of the olefin-lean retentate stream is introduced to a lower portion of the absorption column below the upper portion Element 32: wherein a retentate-side pressure of the salt ion membrane is at least about 1.5 bar greater than a permeate-side pressure of the salt ion membrane.

Element 33: wherein a single salt ion membrane is used to promote separation of the mixed feed stream.

Element 34: wherein a single absorption device is used to promote olefin extraction into the second aqueous salt stream.

Element 35: wherein the salt ion membrane comprises at least a feed-receiving zone, a membrane material, and a permeate-receiving zone.

By way of non-limiting example, illustrative combinations applicable to A may include, but are not limited to, 1 and/or 2, and 3 and/or 4; 1 and/or 2, and 5; 1 and/or 2, and 6; 1 and/or 2, and 7; 1 and/or 2, 7 and 8; 1 and/or 2, 7 and 9; 1 and/or 2, 7, 9 and 10; 1 and/or 2, 7, 9 and 11; 1 and/or 2, 7, 9, 11 and 12; 1 and/or 2, 7 and 13; 1 and/or 2, 7, 13 and 14; 1 and/or 2, 7, and 13-15; 1 and/or 2, 7, 13 and 16; 1 and/or 2, 7 and 17; 1 and/or 2, 7 and 18; 1 and/or 2, 18 and 19; 1 and/or 2, and 20; 1 and/or 2, and 21; 1 and/or 2, and 22; 1 and/or 2, and 23; 1 and/or 2, 21 and 23; 1 and/or 2, and 24; 1 and/or 2, and 25; 1 and/or 2, and 26; 1 and/or 2, and 27; 1 and/or 2, and 28; 1 and/or 2, and 29; 1 and/or 2, and 30; 1 and/or 2, and 31; 1 and/or 2, and 32; 1 and/or 2, and 33; 1 and/or 2, and 34; 1 and/or 2, and 35; 3 and/or 4, and 5; 3 and/or 4, and 6; 3 and/or 4, and 7; 3 and/or 4, 7 and 8; 3 and/or 4, 7 and 9; 3 and/or 4, 7, 9 and 10; 3 and/or 4, 7, 9 and 11; 3 and/or 4, 7, 9, 11 and 12; 3 and/or 4, 7 and 13; 3 and/or 4, 13 and 14; 3 and/or 4, and 13-15; 3 and/or 4, 13 and 16; 3 and/or 4, and 17; 3 and/or 4, and 18; 3 and/or 4, 18 and 19; 3 and/or 4, and 20; 3 and/or 4, and 21; 3 and/or 4, and 22; 3 and/or 4, and 23; 3 and/or 4, 21 and 23; 3 and/or 4, and 24; 3 and/or 4, and 25; 3 and/or 4, and 26; 3 and/or 4, and 27; 3 and/or 4, and 28; 3 and/or 4, and 29; 3 and/or 4, and 30; 3 and/or 4, and 31; 3 and/or 4, and 32; 3 and/or 4, and 33; 3 and/or 4, and 34; 3 and/or 4, and 35; 6 and 7; 6-8; 6, 7, 9 and 10; 6, 7, 9 and 11; 6, 7 and 13; 6, 7, 13 and 14; 6, 7 and 13-15; 6, 7, 13 and 16; 6, 7 and 17; 6, 7 and 18; 6, 7, 18 and 19; 6 and 20; 6 and 21; 6 and 22; 6 and 23; 6, 21 and 23; 6 and 24; 6 and 25; 6 and 26; 6 and 27; 6 and 28; 6 and 29; 6 and 30; 6 and 31; 6 and 32; 6 and 33; 6 and 34; 6 and 35; 7 and 8; 7 and 9; 7, 9 and 10; 7, 9 and 11; 7, 9, 11 and 12; 7 and 13; 7, 13 and 14; 7, and 13-15; 7, 13 and 16; 7 and 17; 7 and 18; 7, 18 and 19; 7 and 20; 7 and 21; 7 and 22; 7 and 23; 7, 21 and 23; 7 and 24; 7 and 25; 7 and 26; 7 and 27; 7 and 28; 7 and 29; 7 and 30; 7 and 31; 7 and 32; 7 and 33; 7 and 34; 7 and 35; 11 and 12; 11 and 17; 11 and 18; 11, 18 and 19; 11 and 20; 11 and 21; 11 and 22; 11 and 23; 11, 21 and 23; 11 and 24; 11 and 25; 11 and 26; 11 and 27; 11 and 28; 11 and 29; 11 and 30; 11 and 31; 11 and 32; 11 and 33; 11 and 34; 11 and 35; 17 and 18; 17, 18 and 19; 17 and 20; 17 and 21; 17 and 22; 17 and 23; 17, 21 and 23; 17 and 24; 17 and 25; 17 and 26; 17 and 27; 17 and 28; 17 and 29; 17 and 30; 17 and 31; 17 and 32; 17 and 33; 17 and 34; 17 and 35; 18 and 19; 18 and 20; 18 and 21; 18 and 22; 18 and 23; 18, 21 and 23; 18 and 24; 18 and 25; 18 and 26; 18 and 27; 18 and 28; 18 and 29; 18 and 30; 18 and 31; 18 and 32; 18 and 33; 18 and 34; 18 and 35; 20 and 21; 20 and 22; 20 and 23; 20, 21 and 23; 20 and 24; 20 and 25; 20 and 26; 20 and 27; 20 and 28; 20 and 29; 20 and 30; 20 and 31; 20 and 32; 20 and 33; 20 and 34; 20 and 35; 21 and 22; 21 and 23; 21 and 24; 21 and 25; 21 and 26; 21 and 27; 21 and 28; 21 and 29; 21 and 30; 21 and 31; 21 and 32; 21 and 33; 21 and 34; 21 and 35; 22 and 23; 22 and 24; 22 and 25; 22 and 26; 22 and 27; 22 and 28; 22 and 29; 22 and 30; 22 and 31; 22 and 32; 22 and 33; 22 and 34; 22 and 35; 23 and 24; 23 and 25; 23 and 26; 23 and 27; 23 and 28; 23 and 29; 23 and 30; 23 and 31; 23 and 32; 23 and 33; 23 and 34; 23 and 35; 24 and 25; 24 and 26; 24 and 27; 24 and 28; 24 and 29; 24 and 30; 24 and 31; 24 and 32; 24 and 33; 24 and 34; 24 and 35; 25 and 26; 25 and 27; 25 and 28; 25 and 29; 25 and 30; 25 and 31; 25 and 32; 25 and 33; 25 and 34; 25 and 35; 26 and 27; 26 and 28; 26 and 29; 26 and 30; 26 and 31; 26 and 32; 26 and 33; 26 and 34; 26 and 35; 27 and 28; 27 and 29; 27 and 30; 27 and 31; 27 and 32; 27 and 33; 27 and 34; 27 and 35; 28 and 29; 28 and 30; 28 and 31; 28 and 32; 28 and 33; 28 and 34; 28 and 35; 29 and 30; 29 and 31; 29 and 32; 29 and 33; 29 and 34; 29 and 35; 30 and 31; 30 and 32; 30 and 33; 30 and 34; 30 and 35; 31 and 32; 31 and 33; 31 and 34; 31 and 35; 32 and 33; 32 and 34; 32 and 35; 33 and 34; 34 and 35; and 34 and 35.

The present disclosure further relates to the following non-limiting embodiments:

A1: A process comprising: A process comprising:

providing a mixed feed stream comprising at least one olefin and at least one paraffin;

introducing at least a first portion of the mixed feed stream and a first aqueous salt stream to a salt ion membrane under conditions effective to form at least two phases while contacting the salt ion membrane;

wherein the salt ion membrane is more permeable to olefins than to paraffins;

obtaining an olefin-rich permeate stream and an olefin-lean retentate stream from the salt ion membrane, the olefin-lean retentate stream comprising at least a portion of the at least one olefin from the mixed feed stream;

wherein at least one of the olefin-rich permeate stream and the olefin-lean retentate stream further comprises a salt ion membrane aqueous salt phase;

introducing at least a portion of the olefin-lean retentate stream and a second aqueous salt stream to an absorption device under conditions effective to promote olefin extraction into the second aqueous salt stream;

obtaining from the absorption device an olefin-rich aqueous salt stream comprising at least a portion of the at least one olefin from the olefin-lean retentate stream, and an olefin-lean hydrocarbon stream comprising at least a portion of the at least one paraffin from the mixed feed stream; and providing at least a portion of the olefin-rich aqueous salt stream as at least a portion of the first aqueous salt stream.

A2: The process of A1, wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream.

A3: The process of A2, wherein a makeup stream comprising an aqueous salt solution or water is supplied as at least a portion of the second aqueous salt stream.

A4: The process of A2 or A3, wherein the olefin-rich permeate stream further comprises at least a portion of the salt ion membrane aqueous salt phase, and at least a portion of the second aqueous salt stream is obtained from the salt ion membrane aqueous salt phase comprising the olefin-rich permeate stream.

A5: The process of any of A2 to A4, wherein the olefin-lean retentate stream comprises at least a portion of the salt ion membrane aqueous salt phase, and at least a portion of the second aqueous salt stream is obtained from the salt ion membrane aqueous salt phase comprising the olefin-lean retentate stream.

A6: The process of any of A2 to A5, wherein a first portion of the salt ion membrane aqueous salt phase is diverted away from a second portion of the salt ion membrane aqueous salt phase being provided to the absorption device.

A7: The process of any of A1 to A6, wherein the second aqueous salt stream has a lower olefin concentration than does the first aqueous salt stream.

A8: The process of A7, wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream, and the process further comprising:

performing a conditioning operation upon at least a portion of the salt ion membrane aqueous salt phase to produce the lower olefin concentration.

A9: The process of A8, wherein the conditioning operation comprises at least one action performed on the salt ion membrane aqueous salt phase selected from the group consisting of a temperature change, a pressure change, a phase separation, and any combination thereof.

A10: The process of A8 or A9, wherein the conditioning operation comprises at least phase separation of the salt ion membrane aqueous salt phase from a conditioned hydrocarbon-rich stream comprising one or more olefins.

A11: The process of A10, further comprising:

introducing at least a portion of the conditioned hydrocarbon-rich stream to the salt ion membrane.

A12: The process of A10 or A11, wherein the salt ion membrane aqueous salt phase is separated from the conditioned hydrocarbon-rich stream as a hydrocarbon-lean stream, and at least a portion of the hydrocarbon-lean stream is provided to the absorption device as at least a portion of the second aqueous salt stream.

A13: The process of A12, wherein at least a portion of the hydrocarbon-lean stream is diverted away from the absorption device as a purge stream or a product stream.

A14: The process of any of A10 to A13, wherein the conditioning operation comprises changing a temperature of the salt ion membrane aqueous salt phase at least once.

A15: The process of A14, wherein changing the temperature of the salt ion membrane aqueous salt phase at least once comprises:

raising the temperature of the salt ion membrane aqueous salt phase from a first temperature to a second temperature to lower an olefin absorption capacity thereof;

after raising the temperature of the salt ion membrane aqueous salt phase to the second temperature, performing phase separation to separate the conditioned hydrocarbon-rich stream from the salt ion membrane aqueous salt phase; and after separating the conditioned hydrocarbon-rich stream from the salt ion membrane aqueous salt phase, lowering the temperature of the salt ion membrane aqueous salt phase from the second temperature to a third temperature to at least partially restore the olefin absorption capacity.

A16: The process of A15, wherein the first temperature and the third temperature are about equal.

A17: The process of A15 or A16, further comprising:

performing a first phase separation prior to raising the temperature and separating a first conditioned hydrocarbon-rich stream comprising one or more olefins from the salt ion membrane aqueous salt phase.

A18: The process of any of A15 to A17, further comprising:

performing phase separation upon the olefin-lean retentate stream and separating an olefin-lean hydrocarbon-rich stream from the salt ion membrane aqueous salt phase prior to raising the temperature of the salt ion membrane aqueous salt phase; and introducing at least a portion of the olefin-lean hydrocarbon rich stream to the absorption device.

A19: The process of any of A9 to A18, further comprising: raising pressure of the salt ion membrane aqueous salt phase prior to providing the salt ion membrane aqueous salt phase as at least a portion of the second aqueous salt stream.

A20: The process of any of A9 to A19, wherein at least a portion of the salt ion membrane aqueous salt phase is diverted away from the absorption device as a purge stream or a product stream.

A21: The process of any of A1 to A20, further comprising: introducing at least a second portion of the mixed feed stream to the absorption device.

A22: The process of any of A1 to A21, wherein the first and second aqueous salt streams comprise a silver (I) salt, a copper (I) salt, or any combination thereof.

A23: The process of any of A1 to A22, wherein the first and second aqueous salt streams comprise silver nitrate.

A24: The process of any of A1 to A23, wherein the salt ion membrane and the first and second aqueous salt streams each comprise one or more metal salts that are the same.

A25: The process of any of A1 to A24, wherein one or more olefins are obtained from the olefin-rich permeate stream at a purity of at least about 95 wt %, based on total hydrocarbons in the olefin-rich permeate stream.

A26: The process of any of A1 to A25, wherein the olefin-rich permeate stream contains at least about 95 wt % of the one or more olefins in the mixed feed stream, based on total olefins in the mixed feed stream.

A27: The process of any of A1 to A26, wherein an equal number of the salt ion membrane and the absorption device are present.

A28: The process of any of A1 to A27, wherein the olefin-rich permeate stream is obtained at a pressure of at least about 1.5 bar.

A29: The process of any of A1 to A28, wherein the absorption device is selected from the group consisting of an absorption column, a rotating packed bed, and a compact contacting unit.

A30: The process of any of A1 to A29, wherein the absorption device comprises an absorption column, the second aqueous salt stream is introduced to an upper portion of the absorption column and the at least a portion of the olefin-lean retentate stream is introduced to the absorption column below the second aqueous salt stream.

A31: The process of A30, wherein the absorption column comprises at least an absorber top settling zone, an absorber bottom settling zone, and an internals zone between the absorber top settling zone and the absorber bottom settling zone.

A32: The process of A30 or A31, wherein the at least a portion of the olefin-lean retentate stream is introduced to a lower portion of the absorption column below the upper portion A33: The process of any of A1 to A32, wherein a retentate-side pressure of the salt ion membrane is at least about 1.5 bar greater than a permeate-side pressure of the salt ion membrane.

A34: The process of any of A1 to A33, wherein a single salt ion membrane is used to promote separation of the mixed feed stream.

A35: The process of any of A1 to A34, wherein a single absorption device is used to promote olefin extraction into the second aqueous salt stream.

A36: The process of any of A1 to A35, wherein the salt ion membrane comprises at least a feed-receiving zone, a membrane material, and a permeate-receiving zone.

Many alterations, modifications, and variations will be apparent to one having ordinary skill in the art in light of the foregoing description without departing from the spirit or scope of the present disclosure and that when numerical limits and numerical upper limits are listed herein, ranges from any lower limit to any upper limit are contemplated.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A process comprising:
providing a mixed feed stream comprising at least one olefin and at least one paraffin;
introducing at least a first portion of the mixed feed stream and a first aqueous salt stream to a salt ion membrane under conditions effective to form at least two phases while contacting the salt ion membrane;
wherein the salt ion membrane is more permeable to olefins than to paraffins;
obtaining an olefin-rich permeate stream and an olefin-lean retentate stream from the salt ion membrane, the olefin-lean retentate stream comprising at least a portion of the at least one olefin from the mixed feed stream;
wherein at least one of the olefin-rich permeate stream and the olefin-lean retentate stream further comprises a salt ion membrane aqueous salt phase;
introducing at least a portion of the olefin-lean retentate stream and a second aqueous salt stream to an absorption device under conditions effective to promote olefin extraction into the second aqueous salt stream;
obtaining from the absorption device an olefin-rich aqueous salt stream comprising at least a portion of the at least one olefin from the olefin-lean retentate stream, and an olefin-lean hydrocarbon stream comprising at least a portion of the at least one paraffin from the mixed feed stream; and
providing at least a portion of the olefin-rich aqueous salt stream as at least a portion of the first aqueous salt stream.

2. The process of claim 1, wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream.

3. The process of claim 2, wherein a makeup stream comprising an aqueous salt solution or water is supplied as at least a portion of the second aqueous salt stream.

4. The process of claim 2, wherein the olefin-rich permeate stream further comprises at least a portion of the salt ion membrane aqueous salt phase, and at least a portion of the second aqueous salt stream is obtained from the salt ion membrane aqueous salt phase comprising the olefin-rich permeate stream.

5. The process of claim 2, wherein the olefin-lean retentate stream comprises at least a portion of the salt ion membrane aqueous salt phase, and at least a portion of the second aqueous salt stream is obtained from the salt ion membrane aqueous salt phase comprising the olefin-lean retentate stream.

6. The process of claim 2, wherein a first portion of the salt ion membrane aqueous salt phase is diverted away from a second portion of the salt ion membrane aqueous salt phase being provided to the absorption device.

7. The process of claim 1, wherein the second aqueous salt stream has a lower olefin concentration than does the first aqueous salt stream.

8. The process of claim 7, wherein the second aqueous salt stream comprises at least a portion of the salt ion membrane aqueous salt phase, the salt ion membrane aqueous salt phase being separated from the olefin-rich permeate stream and/or the olefin-lean retentate stream before being provided as the at least a portion of the second aqueous salt stream, and the process further comprising:
performing a conditioning operation upon at least a portion of the salt ion membrane aqueous salt phase to produce the lower olefin concentration.

9. The process of claim 8, wherein the conditioning operation comprises at least one action performed on the salt ion membrane aqueous salt phase selected from the group consisting of a temperature change, a pressure change, a phase separation, and any combination thereof.

10. The process of claim 8, wherein the conditioning operation comprises at least phase separation of the salt ion membrane aqueous salt phase from a conditioned hydrocarbon-rich stream comprising one or more olefins.

11. The process of claim 10, further comprising:
introducing at least a portion of the conditioned hydrocarbon-rich stream to the salt ion membrane.

12. The process of claim 10, wherein the salt ion membrane aqueous salt phase is separated from the conditioned hydrocarbon-rich stream as a hydrocarbon-lean stream, and at least a portion of the hydrocarbon-lean stream is provided to the absorption device as at least a portion of the second aqueous salt stream.

13. The process of claim 10, wherein the conditioning operation comprises changing a temperature of the salt ion membrane aqueous salt phase at least once.

14. The process of claim 13, wherein changing the temperature of the salt ion membrane aqueous salt phase at least once comprises:
raising the temperature of the salt ion membrane aqueous salt phase from a first temperature to a second temperature to lower an olefin absorption capacity thereof;
after raising the temperature of the salt ion membrane aqueous salt phase to the second temperature, performing phase separation to separate the conditioned hydrocarbon-rich stream from the salt ion membrane aqueous salt phase; and
after separating the conditioned hydrocarbon-rich stream from the salt ion membrane aqueous salt phase, lowering the temperature of the salt ion membrane aqueous salt phase from the second temperature to a third temperature to at least partially restore the olefin absorption capacity.

15. The process of claim 14, further comprising:
performing a first phase separation prior to raising the temperature and separating a first conditioned hydrocarbon-rich stream comprising one or more olefins from the salt ion membrane aqueous salt phase.

16. The process of claim 15, further comprising:
performing phase separation upon the olefin-lean retentate stream and separating an olefin-lean hydrocarbon-rich stream from the salt ion membrane aqueous salt phase prior to raising the temperature of the salt ion membrane aqueous salt phase; and introducing at least a portion of the olefin-lean hydrocarbon rich stream to the absorption device.

17. The process of claim 9, further comprising:

raising pressure of the salt ion membrane aqueous salt phase prior to providing the salt ion membrane aqueous salt phase as at least a portion of the second aqueous salt stream.

18. The process of claim 1, further comprising:

introducing at least a second portion of the mixed feed stream to the absorption device.

19. The process of claim 1, wherein the first and second aqueous salt streams comprise a silver (I) salt, a copper (I) salt, or any combination thereof.

20. The process of claim 1, wherein the salt ion membrane and the first and second aqueous salt streams each comprise one or more metal salts that are the same.

21. The process of claim 1, wherein one or more olefins are obtained from the olefin-rich permeate stream at a purity of at least about 95 wt %, based on total hydrocarbons in the olefin-rich permeate stream.

22. The process of claim 1, wherein the olefin-rich permeate stream contains at least about 95 wt % of the one or more olefins in the mixed feed stream, based on total olefins in the mixed feed stream.

23. The process of claim 1, wherein an equal number of the salt ion membrane and the absorption device are present.

24. The process of claim 1, wherein the absorption device is selected from the group consisting of an absorption column, a rotating packed bed, and a compact contacting unit.

25. The process of claim 1, wherein a retentate-side pressure of the salt ion membrane is at least about 1.5 bar greater than a permeate-side pressure of the salt ion membrane.

26. The process of claim 1, wherein a single salt ion membrane is used to promote separation of the mixed feed stream.

27. The process of claim 1, wherein a single absorption device is used to promote olefin extraction into the second aqueous salt stream.

* * * * *